United States Patent
Lavon Ben Moshe et al.

(10) Patent No.: US 11,478,453 B2
(45) Date of Patent: Oct. 25, 2022

(54) TREATMENT FOR GLIOBLASTOMA

(71) Applicant: HADASIT MEDICAL RESEARCH SERVICES AND DEVELOPMENT LTD., Jerusalem (IL)

(72) Inventors: Iris Lavon Ben Moshe, Kfar-Saba (IL); Tamar Canello Avramovitch, Rehovot (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 80 days.

(21) Appl. No.: 16/318,468

(22) PCT Filed: Jul. 20, 2017

(86) PCT No.: PCT/IL2017/050819
§ 371 (c)(1),
(2) Date: Jan. 17, 2019

(87) PCT Pub. No.: WO2018/015958
PCT Pub. Date: Jan. 25, 2018

(65) Prior Publication Data
US 2019/0240199 A1 Aug. 8, 2019

Related U.S. Application Data

(60) Provisional application No. 62/364,874, filed on Jul. 21, 2016, provisional application No. 62/419,981, filed on Nov. 10, 2016.

(51) Int. Cl.
*A61K 31/4166* (2006.01)
*A61K 31/175* (2006.01)
*A61K 31/517* (2006.01)
*G01N 33/574* (2006.01)
*A61P 35/00* (2006.01)
*A61K 45/06* (2006.01)
*G01N 33/50* (2006.01)

(52) U.S. Cl.
CPC ........ *A61K 31/4166* (2013.01); *A61K 31/175* (2013.01); *A61K 31/517* (2013.01); *A61K 45/06* (2013.01); *A61P 35/00* (2018.01); *G01N 33/5011* (2013.01); *G01N 33/57407* (2013.01); *G01N 2800/52* (2013.01)

(58) Field of Classification Search
CPC .............. A61K 31/4166; A61K 31/175; A61K 31/517; A61K 45/06; A61K 2300/00; A61P 35/00
See application file for complete search history.

(56) References Cited

U.S. PATENT DOCUMENTS

| 7,709,517 B2 | 5/2010 | Sawyers |
| 8,841,422 B2 | 9/2014 | Qiu |
| 2007/0004753 A1 | 1/2007 | Sawyers |
| 2012/0040914 A1 | 2/2012 | Singh |
| 2014/0100256 A1 | 4/2014 | Lorenz |
| 2014/0255471 A1* | 9/2014 | Gmeiner .................. A61K 9/19 424/450 |
| 2014/0329786 A1 | 11/2014 | Davies |
| 2015/0210649 A1 | 7/2015 | Dwivedi |
| 2015/0239848 A1 | 8/2015 | Peddy |
| 2015/0265587 A1 | 9/2015 | Balbas |

FOREIGN PATENT DOCUMENTS

| EP | 3062106 A1 | 8/2016 |
| WO | 8304019 A1 | 11/1983 |
| WO | 0176586 A1 | 10/2001 |
| WO | 2011050353 A1 | 4/2011 |
| WO | 2015049650 A1 | 4/2015 |
| WO | 2016170102 A1 | 10/2016 |

OTHER PUBLICATIONS

Friedman. Temozolomide in early stages of newly diagnosed malignant glioma and neoplastic meningitis. Seminars in Oncology (2000), 27(3, Suppl. 6), 35-40 ISSN:0093-7754, abstract.*
Adams et al., (1990) Hormonal dependency of cerebral meningiomas. Part 2: In vitro effect of steroids, bromocriptine, and epidermal growth factor on growth of meningiomas. J Neurosurg 73(5): 750-755.
Bassetto et al., (2016) Design and synthesis of novel bicalutamide and enzalutamide derivatives as antiproliferative agents for the treatment of prostate cancer. Eur J Med Chem 118: 230-243.
Bing et al., (2015) DHT inhibits the Aβ25-35-induced apoptosis by regulation of seladin-1, survivin, XIAP, bax, and bcl-xl expression through a rapid PI3-K/Akt signaling in C6 glial cell lines. Neurochem Res 40(1): 41-48.
Carroll et al., (1995) Androgen receptor expression in meningiomas. J Neurosurg 82(3): 453-460.
Carroll et al., (1995) Steroid hormone receptors in astrocytic neoplasms. Neurosurgery 37(3): 496-503; discussion 503-4.
Chua and Bristow (2016) Testosterone in Androgen Receptor Signaling and DNA Repair: Enemy or Frenemy? Clin Cancer Res 22(13): 3124-3126.
Chung et al., (1996) Expression of androgen receptors in astrocytoma. J Korean Med Sci 11(6): 517-521.

(Continued)

*Primary Examiner* — Barbara P Badio
(74) *Attorney, Agent, or Firm* — Rodney J. Fuller; Booth Udall Fuller, PLC

(57) ABSTRACT

The invention relates to the treatment of brain tumors, specifically to improved therapy for glioblastoma utilizing specific endocrine modulators and drug combinations. The compositions and uses thereof according to the invention employ androgen receptor (AR) inhibitors, either alone or in combination with receptor tyrosine kinase inhibitors and/or chemotherapeutic agents. According to certain advantageous embodiments, the use of the AR inhibitor enzalutamide, optionally in combination with epidermal growth factor receptor inhibitors such as erlotinib and alkylating agents such as carmustine and temozolomide, is contemplated.

12 Claims, 19 Drawing Sheets
Specification includes a Sequence Listing.

(56) References Cited

OTHER PUBLICATIONS

Davey and Grossmann (2016) Androgen Receptor Structure, Function and Biology: From Bench to Bedside. Clin Biochem Rev 37(1): 3-15.
Gatson and Singh (2007) Activation of a membrane-associated androgen receptor promotes cell death in primary cortical astrocytes. Endocrinology 148(5): 2458-2464.
Hickey et al., (2015) Expression of androgen receptor splice variants in clinical breast cancers. Oncotarget 6(42): 44728-44744.
Kerkhof and Vecht (2013) Seizure characteristics and prognostic factors of gliomas. Epilepsia 54(Suppl 9): 12-17.
Lu and Luo (2013) Decoding the androgen receptor splice variants. Transl Androl Urol 2(3): 178-186.
Maxwell et al., (1993) Expression of androgen and progesterone receptors in primary human meningiomas. J Neurosurg 78(3): 456-462.
Murat et al., (2008) Stem cell-related "self-renewal" signature and high epidermal growth factor receptor expression associated with resistance to concomitant chemoradiotherapy in glioblastoma. J Clin Oncol 26(18): 3015-3024.
Prados et al., (2009) Phase II study of eriotinib plus temozolomide during and after radiation therapy in patients with newly diagnosed glioblastoma multiforme or gliosarcoma. J Clin Oncol 27(4): 579-584.
Reardon et al., (2015) Phase I/randomized phase II study of afatinib, an irreversible ErbB family blocker, with or without protracted temozolomide in adults with recurrent glioblastoma. Neuro Oncol 17(3): 430-439.
Rodriguez-Vida et al., (2015) Enzalutamide for the treatment of metastatic castration-resistant prostate cancer. Drug Des Devel Ther 9: 3325-3339.
Sun et al., (2006) Neuronal and glioma-derived stem cell factor induces angiogenesis within the brain. Cancer Cell 9(4): 287-300.
Sun et al., (2017) Androgen Receptor Regulates the Growth of Neuroblastoma Cells in vitro and in vivo. Front Neurosci 11: 116; 11 pages.
Tan et al., (2015) Androgen receptor: structure, role in prostate cancer and drug discovery. Acta Pharmacol Sin 36(1): 3-23.
Vanaja et al., (2003) Transcriptional silencing of zinc finger protein 185 identified by expression profiling is associated with prostate cancer progression. Cancer Res 63(14): 3877-3882.
Wadosky and Koochekpour (2016) Therapeutic Rationales, Progresses, Failures, and Future Directions for Advanced Prostate Cancer. Int J Biol Sci 12(4): 409-426.
Watson et al., (2002) Molecular characterization of human meningiomas by gene expression profiling using high-density oligonucleotide microarrays. Am J Pathol 161(2): 665-672.
Wick et al., (2011) Pathway inhibition: emerging molecular targets for treating glioblastoma. Neuro Oncol 13(6): 566-579.
Yu et al., (2004) Gene expression alterations in prostate cancer predicting tumor aggression and preceding development of malignancy. J Clin Oncol 22(14): 2790-2799.
Yu et al., (2015) Androgen receptor signaling regulates growth of glioblastoma multiforme in men. Tumour Biol 36(2): 967-972.
Androgen receptor variant 5,6,7es [*Homo sapiens*]; ACZ81436.1. Dated Dec. 14, 2009 (Dec. 14, 2009). Retrieved on May 2, 2019 from: https://www.ncbi.nlm.nih.gov/protein/ACZ81436.1/; 2 pages.
*Homo sapiens* androgen receptor (AR), transcript variant 1, mRNA; NM_000044. Dated Jul. 9, 2016 (Jul. 9, 2016). Retrieved on May 2, 2019 from: https://www.ncbi.nlm.nih.gov/nuccore/NM_000044.3; 5 pages.
*Homo sapiens* androgen receptor (AR), transcript variant 3, mRNA; NM_001348061.1. Dated Apr. 15, 2019 (Apr. 15, 2019). Retrieved on May 2, 2019 from: https://www.ncbi.nlm.nih.gov/nuccore/NM_001348061.1/; 5 pages.
*Homo sapiens* androgen receptor splice variant 3 (AR) mRNA, complete cds, alternatively spliced; FJ235916. Dated May 27, 2015 (May 27, 2015). Retrieved on May 2, 2019 from: https://www.ncbi.nlm.nih.gov/nuccore/FJ235916.1/; 2 pages.
*Homo sapiens* chromosome X, GRCh38.p12 Primary Assembly; NC_000023.11. Dated Mar. 26, 2018 (Mar. 26, 2018). Retrieved on May 2, 2019 from: https://www.ncbi.nlm.nih.gov/nuccore/568815575/; 40 pages.
Peereboom et al., (2010) Phase II trial of erlotinib with temozolomide and radiation in patients with newly diagnosed glioblastoma multiforme. J Neurooncol 98(1): 93-99.
Afuresertib; PubChem CID 46843057, CAS No. 1047644-62-1. Created on Aug. 16, 2010; Modified Jul. 3, 2021. 24 pages.
Chao et al., (1996) Phase II study of flutamide in the treatment of hepatocellular carcinoma. Cancer 77(4): 635-639.
Liu et al., (2014) Expression of estrogen receptors, androgen receptor and steroid receptor coactivator-3 is negatively correlated to the differentiation of astrocytic tumors. Cancer Epidemiol 38(3): 291-297.
Llovet (2005) Updated treatment approach to hepatocellular carcinoma. J Gastroenterol 40(3): 225-235.

\* cited by examiner

TREATMENT FOR GLIOBLASTOMA

FIELD OF THE INVENTION

The invention relates to the treatment of cancer. Specifically, the invention is directed to the use of endocrine modulators and drug combinations in providing improved therapy for patients afflicted with brain tumors such as glioblastomas.

BACKGROUND OF THE INVENTION

Glioblastoma multiforme (GBM, also known as glioblastoma and grade IV astrocytoma) is an extremely aggressive tumor. Symptoms are similar to those of other brain tumors, and may include seizure, nausea and vomiting, headache, memory loss, hemiparesis, and progressive memory, personality, or neurological deficit due to temporal and frontal lobe involvement. Although any brain tumor can cause seizures, their development is most commonly associated with neuroepithelial tumors, including GBM. The incidence of epilepsy in patients with GBM varies between 30% and 62%, in about two thirds as presenting symptom and in one third developing during the course of the disease (Kerkhof et al., 2013).

It is very difficult to treat glioblastomas due to several complicating factors. GBM tumor cells are generally very resistant to conventional therapies. These tumors contain many different types of cells, wherein some cells may respond well to certain therapies, while others may not be affected at all. Another complicating factor is that normal brain cells are relatively susceptible to damage due to conventional therapy, and the brain has a very limited capacity to repair itself compared to other organs. The fact that many drugs cannot cross the blood-brain barrier to act on the tumor further limits the range of chemotherapies suitable for treating GBM patients.

Treatment for GBM typically involves surgery and radiation therapy, and the alkylating agent temozolomide may be used as part of the first-line treatment. However, even with combined chemoradiation using temozolomide, the median survival is only 14.6 months. Thus, new therapeutic targets and improved modalities for the treatment of GBM are required.

Androgen Receptors

Androgens and androgen receptors (AR) play a pivotal role in expression of the male phenotype. Several diseases, such as androgen insensitivity syndrome and prostate cancer (PC), are associated with alterations in AR functions. Indeed, androgen blockade by drugs that prevent the production of androgens (androgen deprivation therapy) and/or block the action of the AR (AR antagonists), is routinely used to inhibit prostate cancer growth. However, resistance to these drugs often occurs within 2-3 years as the patients develop castration-resistant prostate cancer (CRPC). The resistance is typically associated with AR aberrations, including up-regulation of its expression, amplification of the AR gene, expression of androgen receptor splice variants, and/or mutations that result in aberrantly active (e.g. ligand-independent) receptors (Wadosky and Koochekpour 2016).

The AR belongs to the steroid hormone group of nuclear receptors. The AR gene (NR3C4, nuclear receptor subfamily 3, group C, gene 4) is mapped to the long arm of the X-chromosome (Xq11-12). The human AR protein is encoded by 8 exons (1-8) and similarly to other nuclear receptors, consists of N-terminal regulatory domain (NTD), DNA-binding domain (DBD), a small hinge region, and ligand binding domain (LBD). The N-terminal regulatory domain mediates most of AR's transcriptional activity. Two isoforms of AR (87 kDa and 110 kDa) have been identified in which the 87 kDa AR has a truncated N-terminus compared to the full length AR (Wadosky and Koochekpour 2016).

Normally, the AR is a ligand-dependent transcription factor that controls the expression of specific genes. It is sequestered in the cytoplasm by heat-shock proteins and co-chaperones. Upon binding to its native ligands 5α-dihydrotestosterone (DHT) or Testosterone, the chaperones dissociate, AR dimerizes and translocates into the nucleus. There, it binds to the androgen response element (ARE) in the promoter region of its target genes, which may vary depending on the type of cell in which AR is expressed. AR has also been reported to exert both positive and negative effects on DNA-repair mechanisms induced by irradiation, depending on specific parameters including dosage and timing of treatment (Lee et al., 2016). Unlike AR (also referred to as "classical" AR, genomic AR or cellular AR), membrane androgen receptors (mARs) are a group of cell surface-expressed, G protein-coupled receptors (GPCRs) that rapidly alter cell signaling via modulation of intracellular signaling cascades. Known or proposed mARs include GPRC6A and ZIPS. While there are some evidences that mARs bind and are activated by testosterone and/or other androgens, some studies showed that agonists, such as R1881 (methyltrienolone) and mibolerone, and antiandrogens, such as flutamide and cyproterone acetate, do not bind to mARs or influence nonclassical androgen actions in many cells. Thus, AR is structurally unrelated to, and functionally distinct from, mARs.

AR splice variants, arising primarily through exon skipping and cryptic exon inclusion and/or structural rearrangements of the AR gene, have variable structures but typically lack all or a portion of the LBD (Wadosky and Koochekpour 2016, Lu et al., 2013). Some splice variants are found in normal tissues, and variants lacking the LBD have been found to be up-regulated in prostate and breast tumors and were shown to be activated in a ligand-independent mechanism. One such truncated form, AR-V7/AR3, has been postulated to be a major androgen-independent driver of AR-regulated gene expression in CRPC. Certain AR splice variants, including inter alia AR3, have been described in U.S. Pat. No. 8,841,422 and EP3062106.

Hickey et al. (2015) have identified AR and variants thereof, including AR-7, in breast cancer cells, and demonstrated by ex vivo experiments that the activity of AR-V7 is not significantly altered by AR antagonists such as enzalutamide. Hickey et al. have also demonstrated that AR-V7 expression is up-regulated by enzalutamide in primary breast tumors. The publication discloses that AR may exert either positive or negative effects on breast tumor cell growth and expansion, depending on the molecular subtype of the tumor and its expression of additional effectors such as estrogen receptor, and further discloses a striking difference in the gene expression profile induced by AR-7 in prostate and breast tumors. The authors further disclose that their data raise a cautionary note for exploring androgen deprivation therapy (e.g. by AR antagonists) in women with breast cancer.

AR ligand-independent activation could be achieved through crosstalk with different signaling pathways. Such pathways include receptor tyrosine kinases (RTKs), e.g. those involving signaling via insulin-like growth factor (IGF), keratinocyte growth factor (KGF), epidermal growth factor receptor (EGFR) or erbB-2 (HER2), as a consequence of activating the downstream effectors, including, but not limited to, phosphoinositol 3 kinase (PI3K)/AKT/mTOR. These AR-independent pathways have been suggested to promote cancer cell survival and growth in prostate cancer (reviewed in Tan, Li et al. 2015).

RTKs such as EGFR also play an important role in regulating cellular growth in many tumors, including gliomas (Wick, Weller et al. 2011). Activation of EGFR results in a downstream PI3K/Akt cascade and facilitates cell survival, proliferation, and migration. Several EGFR inhibitors have been developed as anti-cancer drugs. For example, erlotinib (marketed under the trade name TARCEVA®) is a small molecule EGFR inhibitor indicated for the treatment of locally advanced or metastatic nonsmall cell lung cancer (NSCLC) with EGFR activating mutations, and in combination with gemcitabine for the treatment of patients with metastatic pancreatic cancer. Erlotinib is mainly metabolized by the liver enzyme CYP3A4, and its co-administration of with CYP3A4 inducers should therefore be avoided. As with other ATP competitive small molecule tyrosine kinase inhibitors, patients rapidly develop erlotinib resistance. Afatinib, an irreversible ErbB family blocker (trade name GILOTRIF® in the US and GIOTRIF® in Europe) was recently tested in Phase I/randomized phase II study with or without protracted temozolomide in adults with recurrent glioblastoma. Although afatinib has a manageable safety profile its activity as single-agent in unselected recurrent GBM patients was limited (Reardon, Nabors et al. 2015). In conclusion, response rates to many such inhibitors, including erlotinib and afatinib, were found to be disappointing in GBM patients.

AR is expressed in various cells and tissues, exerting a diverse range of biological actions including in the development and maintenance of the reproductive, musculoskeletal, cardiovascular, immune, neural and haemopoietic systems. AR has also been implicated in the development of certain tumors, including in the prostate, bladder, liver, kidney and lung. AR expression has also been reported in certain other tumors such as meningiomas, with certain discrepancies and controversies as to their potential role in tumorogenesis (Davey & Grossmann, 2016, Maxwell et al. 1993, Carroll et al., 1995b).

AR and Glial Cells

Steroid hormones play a key role in brain development and differentiation. However, the expression and significance of AR in gliomas is controversial. While AR expression, at either the RNA or protein level, has been reported in certain glial tumors, the expression was not found to be associated with altered survival or prognosis. For example, Carroll R S et al. (1995) have observed a 9.6 kb AR mRNA in the majority of astrocytic tumors, while in some tumors they observed a second slightly smaller AR mRNA. They also showed that in 4 out of the 28 patients tested there was a positive immunohistochemistry staining for AR. The publication does not specify whether the expression of AR was higher or lower than in normal brain tissue. Chung Y G et al (1996) have evaluated the expression of AR by immunohistochemistry in 32 astrocytomas, and found that positive AR staining was present in 12 of these cases (38%). The publication further demonstrates that AR expression was not correlated with sex, DNA ploidy pattern or survival, and thus concludes that AR expression is not likely to be correlated with the proliferative potential of glial tumors.

In the central nervous system, androgens can exert either protective or damage-promoting effects. Accordingly, androgens and their receptors were suggested to mediate both positive and negative effects on glial cells in the context of tumor development.

Bing et al. (2015) examined the possible role of androgens in the development of Alzheimer's disease, and found that DHT protected a cultured rat glial cell line from apoptotic death induced by β-amyloid peptides. The protection was mediated in part by the PI3K/Akt signaling. The effect of AR inhibitors was not tested in this system.

Yu et al. (2015) have reported that AR activation by DHT inhibited TGFβ-induced apoptosis and TGFβ receptor signaling in a glioma cell line. The authors have further detected AR overexpression in GBM tissue in adult male subjects, and suggested that their results provided evidence to explain the specific epidemiology of higher incidence of GBM in men.

When glial cell death induced by the alkylating agent iodoacetic acid (IAA) was examined, it was found that AR activation by DHT protected primary cortical astrocytes from IAA-induced cell death. The protection was blocked by the classical AR antagonist flutamide (Gatson et al., 2007). Thus, the use of AR antagonists was found to be associated with damage to healthy brain tissue when combined with chemotherapy by alkylating agents.

US2012040914 discloses a composition for enhancing simultaneously the effectiveness of one or more chemotherapeutic agents and for protecting one or more brain cells, neurons or both, wherein the chemotherapeutic agents treat, ameliorate symptoms, or delay a progression of one or more gliomas comprising: one or more chemotherapeutic agents selected from the group consisting of dacarbazine alkylating agents, salinomycin, temozolomide, procarbazine, nitrosoureas, bis-chloronitrosourea, lomustine, and platinum based chemotherapeutic agents; and one or more membrane androgen receptor (mAR) activating agents and/or agonists selected from the group consisting of testosterone, DHT, methyltestosterone, active metabolites of testosterone, synthetic derivatives of testosterone, C-19 steroids with a side chain at C-17 and two angular methyl groups, and all androgenic derivatives of cyclopentanoperhydrophenanthrene. The publication further refers to methods for treating, ameliorating symptoms, delaying progression or combinations thereof of glioblastoma multiforme.

AR Antagonists

Several AR antagonists have been developed and are mainly used in the treatment of prostate cancer, and include, for example, flutamide, nilutamide, bicalutamide (Casodex) and enzalutamide (XTANDI®, MDV3100). Compositions and methods of manufacturing and using AR antagonists are disclosed, for example, in US2014100256, US2007004753, US2015239848 and US2015210649. Combinations of AR antagonists with Akt inhibitors are disclosed in US2014329786 and WO2015049650.

Bicalutamide is indicated as a means of androgen deprivation therapy for the treatment of stage D2 metastatic prostate cancer in combination with castration (pharmacological with a GnRH analogue or surgical with an orchiectomy) or at a higher dosage as a monotherapy. Though a pure, or silent antagonist of the AR under normal circumstances, bicalutamide, as well as other earlier antiandrogens like flutamide and nilutamide, have been found to possess weak partial agonist properties in the setting of AR overexpression, and agonist activity in the case of certain mutations in the ligand-binding domain of the AR. As both of these circumstances can eventually occur in prostate cancer, resistance to bicalutamide usually develops and the drug has the potential to paradoxically stimulate tumor growth when this happens.

Enzalutamide is a synthetic, non-steroidal pure antiandrogen developed for the treatment of metastatic castration-resistant prostate cancer. As opposed to bicalutamide, enzalutamide does not promote translocation of AR to the cell nucleus and in addition prevents binding of AR to DNA and AR to co-activator proteins. As in other AR antagonists, enzalutamide resistance has been documented upon continuous use. US2015265587 relates to enzalutamide-resistant AR variants, which may contain a mutation that correlates with incidence of castration resistant prostate cancer, selected from F876C, F8761, F876L, F876S, F876V, F876Y, E565K, E588K, S647G, E668K, C686Y, D695E, A699T, R726H, N7271, N771S, H776Y, C784R, and/or K910E. Additional AR variants, described to be resistant to available anti-androgen drugs, are described in U.S. Pat. No. 8,841,422.

Enzalutamide crosses the blood-brain barrier (BBB) and its activity on the brain is associated with the developments of adverse effects. Enzalutamide use in prostate cancer patients was found to be associated with neuropsychiatric adverse events including seizure, memory impairment, and hallucination, wherein predisposing factors included brain metastases. Consequently, enzalutamide is recommended for use in patients lacking central nervous system (CNS) metastases, history of seizure, or who have other predisposing factors which could lower the threshold for seizure (Rodriguez-Vida et al., 2015). Certain enzalutamide-induced adverse events were suggested to be mediated by off-target binding to and inhibition of the GABAA receptor in the CNS.

Enzalutamide is a strong inducer of CYP3A4 and a moderate inducer of CYP2C9 and CYP2C19, and is metabolized by CYP2C8. Accordingly, it is advised to avoid concomitant use of enzalutamide with medicinal products with a narrow therapeutic range that are substrates of CYP3A4, CYP2C9, and CYP2C19, as well as with strong CYP2C8 inhibitors.

Despite the extensive efforts made so far, the median survival time of GBM patients is still very poor, in part due to a lack of adequate therapeutic options. There remains an unmet medical need for effective and safe treatments for brain tumors such as GBM that inhibit tumor development with minimized side effects.

SUMMARY OF THE INVENTION

The invention relates to the treatment of brain tumors, specifically to improved therapy for glioblastoma (GBM) utilizing specific endocrine modulators and drug combinations. Compositions and methods according to embodiments of the invention employ the use of androgen receptor (AR) inhibitors, either alone or in combination with receptor tyrosine kinase (RTK) inhibitors and/or chemotherapeutic agents. According to certain advantageous embodiments, the use of the AR inhibitor enzalutamide, optionally in combination with epidermal growth factor receptor (EGFR) inhibitors such as erlotinib (TARCEVA®) and afatinib (GILOTRIF®) and alkylating agents such as carmustine (BCNU) and temozolomide (TMZ), is contemplated.

The invention is based, in part, on the surprising discovery that genetic alterations at the AR locus are associated with GBM and related brain tumors. Specifically, a genome-wide copy number and loss of heterozygosity array done on DNA extracted from GBM tumor samples from women revealed amplification of the AR region (Xq12) in the majority of the samples, which was often accompanied with loss of heterozygosity (LOH) in the remaining allele. Chromosome inactivation studies done on GBM samples from 35 women revealed that the inactivated allele of this region was lost in 34 samples. Enhanced AR expression at both the mRNA and the protein level was also identified in tumor specimens obtained from male and female patients. In addition, 30% of the samples were unexpectedly found to express an AR splice variant lacking the ligand binding domain (LBD), namely AR variant 7 (AR-7), reported to be associated with the development of castration-resistant prostate cancer (CRPC).

The invention is further based, in part, on the unexpected discovery that incubation with AR antagonists bicalutamide or enzalutamide reduced glioblastoma cell survival, wherein enzalutamide was more effective than bicalutamide in all tested cell lines. The effect was dose-dependent and further varied depending on the expression level of the AR protein. The reduction was also surprisingly demonstrated in GBM cell lines expressing AR-7, as well as in the treatment of xenograft glioblastoma tumors in vivo.

In addition, the invention is based, in part, on the surprising discovery that combinations of the AR antagonists enzalutamide and bicalutamide with RTK antagonist EGFR inhibitors erlotinib or afatinib, optionally further comprising the alkyating agent carmustine, at sub-therapeutic doses, decreased in a synergistic manner the viability of glioblastoma cell lines expressing AR and AR-7.

Accordingly, disclosed herein are improved compositions and methods for the diagnosis and treatment of brain tumors such as glioblastoma multiforme. The compositions and methods of the invention are in some embodiments particularly suitable for, and enable the treatment of, new patient populations, not hitherto considered amenable for treatment by conventional cancer therapy or by hormonal therapy. In other embodiments, advantageous compositions and methods according to the invention provide enhanced efficacy and/or improved safety.

According to some embodiments, the invention relates to methods for the treatment of a brain tumor such as a neuroepithelial tumor in a subject in need thereof. The tumors amenable for treatment according to embodiments of the invention are characterized by AR expression in at least a portion of the tumor cells. In one embodiment the tumor is an astrocytoma. In another embodiment said tumor is a glioma. According to various embodiments, the tumor is selected from the group consisting of glioblastoma, anaplastic astrocytoma, diffuse astrocytoma, oligodendroglioma, anaplastic oligodendroglioma and mixed tumors (e.g. oligoasrocytoma or anaplastic oligoastrocytoma). According to specific embodiments, the tumor is selected from the group consisting of glioblastoma, anaplastic astrocytoma, diffuse astrocytoma, and oligodendroglioma. In a preferred embodiment, said tumor is glioblastoma. According to yet another embodiment, said tumor is meningioma. Each possibility represents a separate embodiment of the invention.

In another embodiment, the tumor is characterized by amplification at the AR gene locus in at least a portion of the tumor cells. According to various embodiments, said amplification is associated with AR gene copy number increase (gain) of at least one, and typically up to 20. In various specific embodiments, said amplification is associated with increase of 1-3, 1-5, 1-10, 1-20, 2-4, 2-6, 5-10 or 5-20 in AR gene copy number. According to yet another embodiment, said tumor is characterized by loss of heterozygosity (LOH) at the AR gene locus in at least a portion of the tumor cells.

According to yet another embodiment, said tumor is characterized by amplification of one allele and LOH at the AR gene locus in at least a portion of the tumor cells.

In another embodiment said tumor is characterized by AR over-expression in at least a portion of the tumor cells. In other embodiments said over-expression is associated with elevation of at least 1.1-fold and typically up to 150 fold in the protein level and/or up to 350,000 fold in the mRNA level (compared to the respective level in non-tumor cells). More typically, said over-expression is associated, in tumors amenable for treatment by the methods of the invention, with elevation of at least 1.1-20 or 1.1-10 fold in the protein and/or mRNA level. In various specific embodiments, said over-expression is associated with elevation of 1.1-2, 1.2-3, 1.3-4, 1.2-1.6, 1.4-5 1.2-20 or 1.3-10 fold in AR protein levels.

In another embodiment said tumor is characterized by expression of at least one AR variant in at least a portion of the tumor cells. In another embodiment the variant is characterized by deletion or mutation at the LBD (for example, due to exon exclusion by alternative splicing). In another embodiment the variant is a ligand-independent AR splice variant. In another embodiment said variant is AR-7. In another embodiment said tumor is characterized by over-expression of wild-type AR and by expression of at least one AR variant in at least a portion of the tumor cells. According to yet another embodiment, said tumor is characterized by expression of at least one AR variant and is further characterized by LOH at the AR gene locus in at least a portion of the tumor cells. In another embodiment said tumor is characterized by expression of AR-V7 and is further characterized by LOH at the AR gene locus, in at least a portion of the tumor cells. In another embodiment said tumor is characterized by over-expression of wild-type AR and by expression of AR-V7 in at least a portion of the tumor cells. In another embodiment said tumor is characterized by over-expression of wild-type AR and AR-V7 in at least a portion of the tumor cells. Each possibility represents a separate embodiment of the invention.

In another embodiment, said tumor is characterized by AR expression (or at least one AR aberration as disclosed herein, e.g. amplification at the AR gene locus, LOH, AR over-expression and/or expression of at least one AR variant) in at least a portion of the tumor cells, and is further characterized by EGFR expression in at least a portion of the tumor cells. In a particular embodiment, said tumor is characterized by expression of AR-V7 and EGFR.

In another embodiment the subject is human. In another embodiment, the subject is female. In another embodiment the subject is male. In another embodiment, said subject is not afflicted with prostate cancer or breast cancer.

In another embodiment, the methods of the invention comprise, or are used for, identifying a subject as amenable for treatment by determining whether the subject is afflicted with a tumor (e.g. GBM or other neuroepithelial tumors) characterized by AR expression in at least a portion of the tumor cells. In another embodiment the methods of the invention comprise identifying the subject as amenable for treatment by determining whether the subject is afflicted with a tumor as disclosed herein, wherein each possibility represents a separate embodiment of the invention.

In another embodiment, the invention relates to a method of determining if a subject afflicted with a brain tumor is amenable for treatment with an AR antagonist or inhibitor, comprising determining the presence of at least one AR aberration selected from the group consisting of: amplification at the AR gene locus, LOH at the AR gene locus, AR over-expression and/or expression of at least one AR variant, in a sample of the subject, wherein the presence of the at least one aberration indicates that said subject is amenable for treatment with the AR antagonist or inhibitor.

In another embodiment said variant is AR-V7. In another embodiment the presence of at least two aberrations indicates that said subject is amenable for treatment. In another embodiment the presence of at least three aberrations indicates that said subject is amenable for treatment. In another embodiment the at least one aberration comprises amplification at the AR gene locus. In another embodiment the amplification is associated with AR gene copy number increase of 1-20. In another embodiment said over-expression is associated with elevation of 1.1-20 folds in the AR protein level. In another embodiment said over-expression is associated with elevation of 1.1-10 folds in the AR mRNA level. In another embodiment the sample is a brain tumor biopsy. In another embodiment the sample is a blood sample. In a particular embodiment said sample is a cell-free blood sample. According to certain embodiments, the methods of the invention comprise administering to the subject in need thereof (e.g. a subject determined to be amenable for treatment as described herein) a therapeutically effective amount of an AR antagonist or inhibitor. In another embodiment the inhibitor is enzalutamide or a derivative thereof. In a particular embodiment said inhibitor is enzalutamide.

While AR inhibitors such as enzalutamide are disclosed herein to be surprisingly effective in the management of GBM when used as a single therapeutic agent, the invention further discloses that such agents may unexpectedly be used in combination with other chemotherapies and anti-cancer agents, with minimized or reduced damage to surrounding tissues and other organs. According to other embodiments, combinations disclosed herein exhibit enhanced and even synergistic effects compared to each treatment alone. According to additional embodiments, the enhanced effects exhibited by the drug combinations disclosed herein provide for their use at lower doses than those acceptable for each drug alone. Thus, the combinations of the invention may be used in some embodiments in patients not amenable for treatment with each drug alone due to impaired safety and/or insufficient efficacy.

According to some embodiment, the AR antagonist or inhibitor is administered in combination (concurrent or sequential) with at least one anti-cancer agent. In various embodiments, the at least one anti-cancer agent is selected from the group consisting of a chemotherapeutic drug, a RTK inhibitor, an immunotherapy (e.g. anti-PD1 antibodies) and an anti-angiogenic therapy (e.g. bevacizumab). In another embodiment the at least one anti-cancer agent comprises a chemotherapeutic drug. In a particular embodiment the chemotherapeutic drug is an alkylating agent, e.g. carmustine or temozolomide. In another embodiment the at least one anti-cancer agent comprises a RTK inhibitor. In a particular embodiment the RTK inhibitor is an EGFR antagonist, e.g. erlotinib or afatinib. In another embodiment said at least one anti-cancer agent comprises at least one chemotherapeutic drug and at least one RTK inhibitor. In another embodiment said at least one anti-cancer agent comprises at least one alkylating agent and at least one EGFR antagonist. In a particular embodiment the methods of the invention comprise administering to the subject enzalutamide in combination with carmustine and erlotinib. In another particular embodiment the methods of the invention comprise administering to the subject enzalutamide in combination with carmustine and afatinib. In other embodiments, the at least one additional anti-cancer agent comprises radiotherapy.

For example, according to embodiments of the invention, a tumor characterized by AR expression (in at least a portion of the tumor cells) may be treated with an AR antagonist or inhibitor as disclosed herein. According to certain embodiments, a tumor characterized by expression of an AR variant characterized by deletion or mutation at the LBD and/or a ligand-independent AR splice variant may be treated by combination therapy as disclosed herein. In a particular example, a tumor characterized by expression of the AR variant (e.g. AR-V7) and EGFR may advantageously be treated by a combination of an AR antagonist or inhibitor (e.g. enzalutamide) and an EGFR antagonist (e.g. erlotinib or afatinib). Accordingly, the methods of the invention may further comprise in some embodiments determining whether the tumor is characterized by expression of EGFR in at least a portion of the tumor cells.

According to other embodiments, the invention relates to compositions and kits comprising, or employing the use of, the combinations of the invention.

In another embodiment, there is provided a therapeutic combination for the treatment of brain tumors, comprising at least one AR antagonist or inhibitor and at least one anti-cancer agent selected from the group consisting of an alkylating agent and a RTK inhibitor. In another embodiment the combination is in the form of a pharmaceutical composition further comprising one or more carriers, excipients or diluents. In another embodiment the composition is formulated for oral administration. In another embodiment there is provided a method of treating a brain tumor characterized by AR expression in at least a portion of the tumor cells in a subject in need thereof, comprising administering to the subject a therapeutic combination according to the invention.

In yet another embodiment, said combination is in the form of a kit further comprising instructions for administering said combination to a subject afflicted with an AR-expressing neuroepithelial tumor, e.g. GBM. Thus, in another embodiment, there is provided a kit for the treatment of an AR-expressing neuroepithelial tumor, comprising an AR inhibitor such as enzalutamide or a derivative thereof, in combination with an alkylating agent and/or an EGFR antagonist. In another embodiment the kit further comprises instructions for administering the AR inhibitor in concurrent or sequential combination with the alkylating agent and/or an EGFR antagonist to a subject afflicted with an AR-expressing neuroepithelial tumor, e.g. glioblastoma.

In another aspect, the invention relates to enzalutamide or a derivative thereof for use in the treatment of a neuroepithelial tumor in a subject in need thereof, wherein the enzalutamide or derivative thereof is used in a therapeutically effective amount and the tumor is characterized by AR expression in at least a portion of the tumor cells.

In one embodiment, said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma. In a particular embodiment said tumor is glioblastoma. In another embodiment said tumor is characterized by: amplification at the AR gene locus, LOH at the AR gene locus, AR over-expression and/or expression of at least one AR variant, in at least a portion of the tumor cells. In another embodiment the amplification is associated with AR gene copy number increase of 1-20. In another embodiment said over-expression is associated with elevation of 1.1-20 fold in the AR protein level. In another embodiment the variant is selected from the group consisting of a variant characterized by deletion or mutation at the LBD and a ligand-independent AR splice variant. In a particular embodiment said variant is AR-V7. In another embodiment, said tumor is characterized by expression of AR-V7 and is further characterized by at least one of: over-expression of wild-type AR, over-expression of AR-V7, and LOH at the AR gene locus, in at least a portion of the tumor cells. In another embodiment the subject is human and/or the subject is female.

In another embodiment the treatment comprises administering to the subject enzalutamide, thereby treating said tumor. In another embodiment the subject is under treatment with at least one additional anti-cancer agent. In another embodiment the at least one additional anti-cancer agent is selected from the group consisting of a chemotherapeutic drug, a RTK inhibitor, an immunotherapy and an anti-angiogenic therapy. In another embodiment the at least one additional anti-cancer agent comprises a chemotherapeutic drug, the chemotherapeutic drug being an alkylating agent. In another embodiment the alkylating agent is selected from the group consisting of temozolomide, carmustine and derivatives and salts thereof. In another embodiment the at least one anti-cancer agent comprises a RTK inhibitor. In another embodiment the RTK inhibitor is an EGFR antagonist. In another embodiment the EGFR antagonist is selected from the group consisting of afatinib, erlotinib and derivatives and salts thereof. In another embodiment said at least one anti-cancer agent comprises at least one alkylating agent and at least one EGFR antagonist.

In another aspect the invention is directed to a therapeutic combination of at least one AR antagonist or inhibitor and at least one anti-cancer agent selected from the group consisting of an alkylating agent and a RTK inhibitor, for use in treating a brain tumor characterized by AR expression in at least a portion of the tumor cells in a subject in need thereof. In another embodiment the AR antagonist or inhibitor is enzalutamide or a derivative thereof, the alkylating agent is selected from the group consisting of temozolomide, carmustine and derivatives and salts thereof, and the RTK inhibitor is selected from the group consisting of afatinib, erlotinib, and derivatives and salts thereof.

In another embodiment said therapeutic combination is in the form of a pharmaceutical composition comprising the at least one AR antagonist or inhibitor and the at least one anti-cancer agent. In another embodiment the AR antagonist or inhibitor is enzalutamide or a derivative thereof, the alkylating agent is selected from the group consisting of temozolomide, carmustine and derivatives and salts thereof, and the RTK inhibitor is selected from the group consisting of afatinib, erlotinib, and derivatives and salts thereof.

In another embodiment said tumor is a glioma. Preferably said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma. More preferably, said tumor is glioblastoma.

In another embodiment said tumor is characterized by amplification at the AR gene locus in at least a portion of the tumor cells. Preferably said tumor is associated with AR gene copy number increase of 1-20. In another embodiment said tumor is characterized by LOH at the AR gene locus in at least a portion of the tumor cells. In another embodiment said tumor is characterized by AR over-expression in at least a portion of the tumor cells. Preferably said tumor is associated with 1.1-20 fold elevation of the AR protein level. In another embodiment said tumor is characterized by expression of at least one AR variant in at least a portion of the tumor cells, wherein the variant is selected from the group consisting of a variant characterized by deletion or mutation at the LBD and a ligand-independent AR splice variant. Preferably said variant is AR-V7. In another embodiment said tumor is characterized by over-expression of wild-type AR and by expression of AR-V7 in at least a portion of the tumor cells, or by over-expression of wild-type AR and over-expression of AR-V7 in at least a portion of the tumor cells. In another embodiment said tumor is characterized by expression of AR-V7 and is further characterized by LOH at the AR gene locus, in at least a portion of the tumor cells. In another embodiment the subject is human and/or the subject is female.

In another aspect there is provided a method of determining if a subject afflicted with a brain tumor is amenable for treatment with an AR antagonist or inhibitor, comprising determining the presence of at least one AR aberration selected from the group consisting of: amplification at the AR gene locus, LOH at the AR gene locus, AR over-expression and/or expression of at least one AR variant, in a sample of the subject, wherein the presence of the at least one aberration indicates that said subject is amenable for treatment with the AR antagonist or inhibitor.

In another embodiment the at least one aberration comprises expression of at least one AR variant selected from the group consisting of an AR variant characterized by deletion or mutation at the LBD and a ligand-independent AR splice variant. Preferably said variant is AR-V7. In another embodiment the presence of at least two aberrations indicates that said subject is amenable for treatment, or the presence of at least three aberrations indicates that said subject is amenable for treatment. In another embodiment the at least one aberration comprises amplification at the AR gene locus. In a particular embodiment the amplification is associated with AR gene copy number increase of 1-20. In another embodiment said over-expression is associated with elevation of 1.1-20 fold in the AR protein level.

In another embodiment the sample is a brain tumor biopsy. In another embodiment the sample is a blood sample. In another embodiment said sample is a cell-free blood sample.

In another embodiment the tumor is a neuroepithelial tumor, preferably an astrocytoma, more preferably a glioma. According to particular embodiments, said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma. In another particular embodiment said tumor is glioblastoma. In yet another embodiment the tumor is meningioma. In another embodiment the subject is human and/or the subject is female.

In another embodiment the invention relates to an AR antagonist or inhibitor for use in tumor treatment in a subject afflicted with a brain tumor, wherein the subject has been determined to be amenable for treatment with the AR antagonist or inhibitor, by a method comprising determining the presence of at least one AR aberration selected from the group consisting of: amplification at the AR gene locus, LOH at the AR gene locus, AR over-expression and/or expression of at least one AR variant, in a sample of the subject, wherein the presence of the at least one aberration indicates that said subject is amenable for treatment with the AR antagonist or inhibitor. In another embodiment said AR antagonist or inhibitor is administered to said subject, thereby treating said tumor in said subject.

In another embodiment the AR antagonist or inhibitor is enzalutamide or a derivative thereof. Preferably said AR antagonist or inhibitor is enzalutamide.

In another embodiment said AR antagonist or inhibitor is adapted for administration in concurrent or sequential combination with at least one additional anti-cancer agent. In another embodiment the at least one anti-cancer agent is selected from the group consisting of an alkylating agent and a RTK inhibitor.

In another embodiment wherein expression of AR-V7 has been determined to be present in the sample, said AR antagonist or inhibitor is for use by administration to said subject in concurrent or sequential combination with at least one additional anti-cancer agent. In another embodiment the at least one anti-cancer agent is selected from the group consisting of an alkylating agent and a RTK inhibitor. In another embodiment the treatment comprises administering to said subject at least one AR antagonist or inhibitor, at least one alkylating agent and at least one RTK inhibitor. In another embodiment said at least one anti-cancer agent is selected from the group consisting of temozolomide, carmustine, afatinib, erlotinib, and derivatives and salts thereof. In another embodiment the AR antagonist or inhibitor is enzalutamide or a derivative thereof. In another embodiment the treatment comprises administering to said subject enzalutamide, carmustine and erlotinib.

In another embodiment said tumor has been further determined to be characterized by EGFR expression in at least a portion of the tumor cells, and the treatment comprises administering to said subject at least one AR antagonist or inhibitor in concurrent or sequential combination with at least one EGFR antagonist. In another embodiment the treatment comprises administering to said subject enzalutamide in concurrent or sequential combination with at least one EGFR antagonist selected from the group consisting of afatinib, erlotinib and derivatives and salts thereof.

In another aspect the invention provides a pharmaceutical composition for the treatment of brain tumors, comprising at least one AR antagonist or inhibitor and at least one anti-cancer agent selected from the group consisting of an alkylating agent and a RTK inhibitor. In another embodiment the composition comprises: (i) enzalutamide, (ii) carmustine or temozolomide, (iii) erlotinib or afatinib, and (iv) one or more carriers, excipients or diluents. In another embodiment said composition is formulated for oral administration.

In another aspect there is provided a kit comprising a combination of at least one AR antagonist or inhibitor and at least one anti-cancer agent selected from the group consisting of an alkylating agent and a RTK inhibitor, further comprising instructions for administering said combination to a subject afflicted with an AR-expressing neuroepithelial tumor. In another embodiment the neuroepithelial tumor is glioblastoma.

Other objects, features and advantages of the present invention will become clear from the following description and drawings.

BRIEF DESCRIPTION OF THE DRAWINGS

FIG. 2A depicts Quantitative PCR (qPCR) analysis of AR mRNA expression following normalization to HPRT in 30 GBM tumor samples and 3 GBM cell lines. FIGS. 2B-2E depict AR RNA expression analyzed using ONCOMINE™. FIG. 2B, GBM AR RNA expression of the TCGA database;

FIG. 2C, GBM AR RNA expression of the Murat cohort; FIG. 2D, glioma AR RNA expression of the Sun cohort; FIG. 2E, meningioma AR RNA expression of the Watson cohort. FIGS. 2F-2G depict analyses of AR expression in prostate carcinoma in the Yu and Vanaja cohorts, respectively.

FIG. 4A: survival of A172 cells.

FIG. 4B: survival of U87MG cells. FIG. 4C: survival of T98G cells. FIG. 4D: survival of PC3 cells. FIG. 4E: Western blot analysis, using sequential probing with either polyclonal antibody against AR (N20) upper lanes; or monoclonal anti-GAPDH (0411) lower lanes, on HEK 293, A172, U87MG and T98G cell lines. FIG. 4F: A cell cycle analysis of glioma cells treated with 10 µM DHT, either alone or with 40 µM or 80 µM enzalutamide, compared to vehicle-treated cells.

FIGS. 6A-6E. Combination therapies of anti-AR signaling agents together with agents that target EGFR in T98G cell line expressing a ligand independent AR splice variant. FIG. 6A: AR variant 7 (A3) was analyzed by qPCR on A172, U87MG and T98G cell lines. FIG. 6B: T98G cells were treated for 72 Hr with DHT (10 µm) and TARCEVA® (erlotinib, "Tra", 1.25-10 µm) with or without 20 µm of bicalutamide (BIC). Cells treated with DHT alone served as a control. Cell viability was determined by Crystal Violet assay and expressed as percentage of cells treated with vehicle. FIG. 6C: T98G cells were treated for 72 Hr with afatinib (Afa, 1.25-5 µm) with or without 20 µm enzalutamide (ENZ), and cell viability was determined and calculated as in FIG. 6B. FIG. 6D: U87MG cells were treated for 72 Hr with 10 µm of DHT alone or in combination with 20 µM bicalutamide (BIC), 2.5 µM of TARCEVA® (erlotinib, "Tra"), with 10 mg/ml of BCNU alone or with a combination of all four agents. Cell viability was determined by Crystal Violet assay and expressed as percentage of cell treated with DHT.

DETAILED DESCRIPTION OF THE INVENTION

Figure 1:
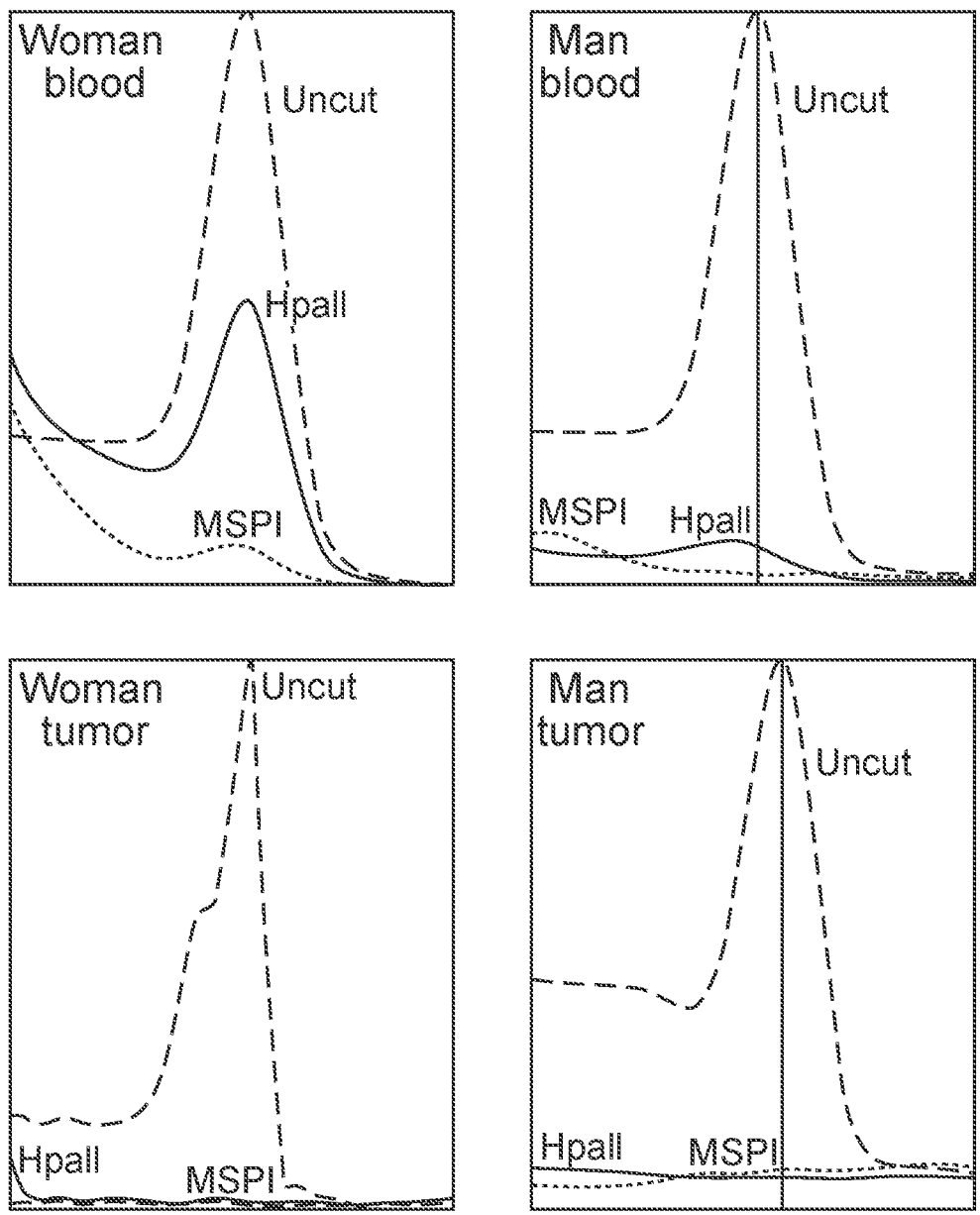
FIG. 1. DNA aberrations in glioblastoma. Chromosome inactivation studies based on the differential methylation patterns in GBM samples from 35 women were performed. The MspI/HpaII pair of isoschizomeric enzymes was used to analyze DNA methylation status at AR locus. AR amplification is demonstrated as melt curve of the amplified amplicon. The amplification of the uncut DNA is compared to those restricted with HpaII/MspI as indicated in the graph.

The invention relates to the treatment of brain tumors, specifically to improved therapy for glioblastoma (GBM) utilizing specific endocrine modulators and drug combinations. Compositions and methods according to embodiments of the invention employ the use of androgen receptor (AR) inhibitors, either alone or in combination with receptor tyrosine kinase (RTK) inhibitors and/or chemotherapeutic agents. According to certain advantageous embodiments, the use of the AR inhibitor enzalutamide, optionally in combination with epidermal growth factor receptor (EGFR) inhibitors such as erlotinib (TARCEVA®) and afatinib and alkylating agents such as carmustine (BCNU) and temozolomide (TMZ), is contemplated.

In one aspect, the invention relates to enzalutamide or a derivative thereof for use in the treatment of a neuroepithelial tumor in a subject in need thereof, wherein the enzalutamide or derivative thereof is used in a therapeutically effective amount and the tumor is characterized by AR expression in at least a portion of the tumor cells.

In another embodiment the invention provided a method for the treatment of a neuroepithelial tumor characterized by AR expression in at least a portion of the tumor cells in a subject in need thereof, comprising administering to the subject a therapeutically effective amount of enzalutamide or a derivative thereof.

In another aspect, the invention relates to a method for the treatment of a glial tumor in a subject in need thereof, comprising administering to the subject a therapeutically effective amount of at least one AR antagonist or inhibitor.

In another aspect, the invention relates to at least one AR antagonist or inhibitor, for use in a method for the treatment of a glial tumor in a subject in need thereof, the method comprising administering to the subject the at least one AR antagonist or inhibitor in a therapeutically effective amount.

In another aspect, there is provided a method of determining if a subject afflicted with a brain tumor is amenable for treatment with an AR antagonist or inhibitor, comprising determining the presence of at least one AR aberration selected from the group consisting of: amplification at the AR gene locus, LOH at the AR gene locus, AR overexpression and/or expression of at least one AR variant, in a sample of the subject, wherein the presence of the at least one aberration indicates that said subject is amenable for treatment with the AR antagonist or inhibitor.

In yet another aspect, the invention is directed to a therapeutic combination for the treatment of brain tumors, comprising at least one AR antagonist or inhibitor and at least one anti-cancer agent selected from the group consisting of an alkylating agent and a RTK inhibitor. In another aspect, the invention provides a pharmaceutical composition for the treatment of brain tumors, comprising at least one AR antagonist or inhibitor and at least one anti-cancer agent selected from the group consisting of an alkylating agent and a RTK inhibitor. In another aspect there is provided a kit comprising a combination of at least one AR antagonist or inhibitor and at least one anti-cancer agent selected from the group consisting of an alkylating agent and a RTK inhibitor, further comprising instructions for administering said combination to a subject afflicted with an AR-expressing neuroepithelial tumor.

Enzalutamide and Other AR Antagonists and Inhibitors

Enzalutamide is an androgen receptor inhibitor of the chemical name 4-{3-[4-cyano-3-(trifluoromethyl)phenyl]-5,5-dimethyl-4-oxo-2-sulfanylideneimidazolidin-1-yl}-2-fluoro-N-methylbenzamide. The structure of enzalutamide is represented by the following formula:

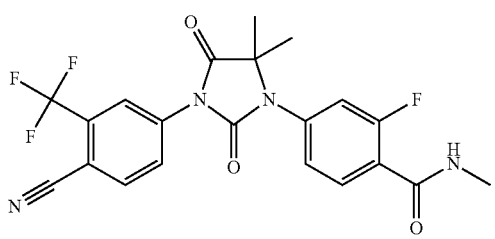 [SMILES: CNC(=O)c1ccc(N2C(=O)N(c3ccc(C#N)c(C(F)(F)F)c3)C(=O)C2(C)C)cc1F]

Enzalutamide is available commercially under the trade name XTANDI®, provided as liquid-filled soft gelatin capsules for oral administration. Each capsule contains 40 mg of enzalutamide as a solution in caprylocaproyl polyoxylglycerides. The inactive ingredients are caprylocaproyl polyoxylglycerides, butylated hydroxyanisole, butylated hydroxytoluene, gelatin, sorbitol sorbitan solution, glycerin, purified water, titanium dioxide, and black iron oxide.

Enzalutamide derivatives have been described, for example in Bassetto et al. (2016) and U.S. Pat. No. 7,709,517, the contents of which are incorporated herein by reference, disclosing certain AR antagonist compounds including enzalutamide derivatives. Enzalutamide derivatives used in the compositions, methods and kits of the invention are structurally and functionally related small molecules, whose chemical structure is based on enzalutamide scaffold with certain substitutions or modifications, that retain the biological functions associated with the activity of enzalutamide as described herein. For example, the substitutions or modifications may include introduction/change of position of trifluoromethyl and trifluoromethoxy groups. Functionally, preferred derivatives are characterized as pure AR antagonists having minimal or no agonistic activities. Enzalutamide derivatives used in embodiments of the invention are pharmacologically equivalent with enzalutamide. In a particular embodiment, the enzalutamide derivative is apalutamide (also known as ARN-509 and JNJ-56021927).

Other embodiments of the invention employ the use of additional compounds, which are specific AR antagonists or inhibitors. As used herein, the term "AR antagonist" or "AR inhibitor" are used interchangeably herein and refer to an agent that specifically inhibits or reduces at least one activity of an AR polypeptide. Exemplary AR activities include, but are not limited to, co-activator binding, DNA binding, ligand binding, and nuclear translocation.

AR antagonists and inhibitors include various agents that inhibit the activity or expression of AR and/or variants thereof. Such agents may include, without limitation, small molecules (e.g. AR antagonists such as enzalutamide and bicalutamide and other agents that inhibit ligand binding and/or AR-mediated transcription), nucleic acids (e.g. RNA interference molecules that inhibit AR expression) and antibodies (e.g. neutralizing antibodies).

Various AR-targeting agents have been described, including, without limitation, bicalutamide, nilutamide, flutamide, cyproterone acetate, spironolactone, drospirenone, enzalutamide, hydroxyflutamide, ARN-509, ASC-J9 and AZD3514. Other AR antagonists or inhibitors are exemplified by the following: BMS 641988, TRC 253 (formerly JNJ-63576253), Galeterone (TOK-001 or VN/124-1), SHR 3680, EPI-506, and Proxalutamide (GT0918).

It should be understood, that preferable agents for use in the compositions and methods of the invention are capable of crossing the blood brain barrier (BBB) following systemic administration. However, other agents may be employed in certain embodiments of the invention, for example for in-situ administration during surgery. For example, bicalutamide has been described as a peripherally-selective antiandrogen that does not cross the BBB, although more recent findings suggest that this drug may also have central functions. According to certain preferable embodiments, said AR antagonist or inhibitor is enzalutamide or a derivative thereof. In a particular embodiment, said AR antagonist or inhibitor is enzalutamide.

Pharmaceutical Compositions, Kits and Therapeutic Combinations

AR antagonists or inhibitors and other anti-cancer agents as described herein (herein referred to as active ingredients) can be administered according to embodiments of the invention in the form of a pharmaceutical composition, further comprising one or more pharmacologically acceptable carriers, excipients or diluents. The purpose of a pharmaceutical composition is to facilitate administration of a compound to an organism. The pharmaceutical compositions may be formulated by one having ordinary skill in the art. Suitable pharmaceutical carriers, including, but not limited to fillers, disintegrants, lubricants, glidants, and soluble and insoluble polymers are described in Remington's Pharmaceutical Sciences, A. Osol, a standard reference text in this field, which is incorporated herein by reference.

For injection, the active ingredients of the pharmaceutical composition may be formulated in aqueous solutions, preferably in physiologically compatible buffers such as Hank's solution, Ringer's solution, or physiological salt buffer. Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

According to some embodiments, enzalutamide or other AR antagonists or inhibitors as described herein may be administered in concurrent or sequential combination with at least one additional anti-cancer agent. According to other embodiments, the invention relates to therapeutic combinations of at least one AR antagonist or inhibitor and at least one anti-cancer agent. According to particular embodiments, the at least one anti-cancer agent is selected from the group consisting of chemotherapeutic agents (e.g. alkylating agents) and RTK inhibitors. These combinations, optionally formulated in the form of a pharmaceutical composition comprising the at least one AR antagonist or inhibitor and at least one anti-cancer agent, may be used in embodiments of the invention as described in further detail below.

According to certain embodiments, there is provided a therapeutic combination of at least one AR antagonist or inhibitor and at least one anti-cancer agent selected from the group consisting of an alkylating agent and a RTK inhibitor, for use in a method for treating a brain tumor characterized by AR expression in at least a portion of the tumor cells in a subject in need thereof. In other embodiments the invention relates to a pharmaceutical composition for the treatment of brain tumors, comprising at least one AR antagonist or inhibitor and at least one anti-cancer agent selected from the group consisting of an alkylating agent and a RTK inhibitor. According to further embodiments, there is provided a kit comprising a combination of at least one AR antagonist or inhibitor and at least one anti-cancer agent selected from the group consisting of an alkylating agent and a RTK inhibitor, further comprising instructions for administering said combination to a subject afflicted with an AR-expressing neuroepithelial tumor.

Advantageously, said AR antagonist or inhibitor is enzalutamide or a derivative thereof. According to particular advantageous embodiments, said AR antagonist or inhibitor is enzalutamide. In another particular embodiment said AR antagonist or inhibitor is selected from the group consisting of enzalutamide, bicalutamide and derivatives thereof. In yet another particular embodiment said AR antagonist or inhibitor is bicalutamide. Each possibility represents a separate embodiment of the invention.

The terms antagonist and inhibitor as used herein with respect to cellular receptors (e.g. RTK or EGFR) refer to molecules having the ability to specifically inhibit a biological function of the respective receptor. Specific inhibition of activity means that other cellular activities not mediated by or associated with the receptor are not substantially inhibited. Typically the inhibitors and antagonists induce a direct inhibiting activity, i.e. by binding to the receptor or its ligand. Other inhibitory agents include those inhibiting the expression of the receptor (e.g. siRNA). Preferred activities specifically inhibited by the antagonists and inhibitors are associated with the development, growth, or spread of a tumor.

The term "receptor tyrosine kinase inhibitor" or "RTK inhibitor" means a compound capable of specifically inhibiting the activity of a member of the RTK family of proteins. A RTK inhibitor can be a small molecule, protein, polypeptide, peptide, nucleic acid, and combinations thereof. Examples of protein targets for RTK inhibitors include, but are not limited to, members of the following RTK families: ephrin receptor, epidermal growth factor receptor, fibroblast growth factor receptor, insulin receptor, insulin-like growth factor receptor (EGFR), neutrophin receptors, platelet-derived growth factor receptor, and vascular endothelial growth factor receptor. A preferred activity inhibited by an RTK inhibitor is associated with the development, growth, or spread of a tumor. Examples of RTK inhibitors include, but are not limited to, afatinib, axitinib, canertinib, cediranib, erlotinib, gefitinib, grandinin, imatinib, lapatinib, leflunomide, lestaurtinib, neratinib, pazopanib, quizartinib, regorafenib, semaxanib, sorafenib, sunitib, sutent, tivozanib, tocerabib, vandetanib, vatalanib, monoclonal antibodies that bind specific RTKs, and combinations thereof.

In some embodiments, the RTK inhibitor is an EGFR antagonist. The term "EGFR inhibitor" or "EGFR antagonist" as used herein refers to a molecule having the ability to specifically inhibit a biological function of a native epidermal growth factor receptor (EGFR). Preferred inhibitors herein specifically interact with (e.g. bind to) an EGFR. A preferred EGFR biological activity inhibited by an EGFR inhibitor is associated with the development, growth, or spread of a tumor. The term is intended to include chemical compounds, such as small molecule inhibitors (e.g., small molecule tyrosine kinase inhibitors) and biologic agents, such as antibodies, interfering RNA (shRNA, siRNA), soluble receptors and the like. EGFR inhibitors that can be used according to the present invention include but are not limited to small molecule inhibitors classified in the art as quinazoline EGFR inhibitors, pyrido-pyrimidine EGFR inhibitors, pyrimido-pyrimidine EGFR inhibitors, pyrrolo-pyrimidine EGFR inhibitors, pyrazolo-pyrimidine EGFR inhibitors, phenylamino-pyrimidine EGFR inhibitors, oxindole EGFR inhibitors, indolocarbazole EGFR inhibitors, phthalazine EGFR inhibitors, isoflavone EGFR inhibitors, quinalone EGFR inhibitors, and tyrphostin EGFR inhibitors. Examples of EGFR inhibitors include, but are not limited to, [6,7-bis(2-methoxyethoxy)-4-quinazolin-4-yl]-(3-ethynylphenyl)amine (also known as OSI-774), erlotinib, CI-1033 (formerly known as PD183805), AG-1478, CGP-59326, PKI-166, EKB-569, lapatinib or lapatinib ditosylate; afatinib, gefitinib, AG490 (a tyrphostin), ARRY-334543, BIBW-2992, EKB-569, ZD6474, BMS-599626 (Bristol-Myers Squibb), cetuximab, panitumumab, and MDX-447.

In certain embodiments, the EGFR antagonist is a small molecule, e.g. erlotinib, afatinib, lapatinib or gefitinib. In a particular embodiment, the EGFR antagonist is selected from the group consisting of afatinib, erlotinib and derivatives and salts thereof. In another particular embodiment, said antagonist is afatinib or erlotinib. Each possibility represents a separate embodiment of the invention.

The term "chemotherapeutic agent" as used herein refers to a cytotoxic or cytostatic chemical or biological substance that can cause death of cancer cells, or specifically interfere with growth, division, repair, and/or function of cancer cells.

The term "alkylating agent" as used in the present specification refers to a chemotherapeutic agent giving an alkyl group in the alkylation reaction in which a hydrogen atom of an organic compound is substituted with an alkyl group, having antitumor activity. This term may be exemplified by nitrogen mustard N-oxide, cyclophosphamide, ifosfamide, melphalan, busulfan, mitobronitol, carboquone, thiotepa, ranimustine, nimustine, temozolomide and carmustine.

As used herein, the term "immunotherapeutic agent" refers to any agent, compound, or biologic which is capable of modulating the host's immune system. An immunotherapeutic agent used in the compositions and methods of the invention is capable of causing a stimulation of the immune system against a tumor cell.

As used herein, the term "anti-angiogenic agent" means a molecule that reduces or prevents angiogenesis, which is the growth and development of blood vessels. Commercially available anti-angiogenic agents include, for example, angiostatin, endostatin and metastatin.

In certain embodiments, the compositions, methods, kits and therapeutic combinations of the invention comprise (or employ the use of) enzalutamide and at least one EGFR antagonist. In a particular embodiment the EGFR antagonist is selected from the group consisting of afatinib, erlotinib and derivatives and salts thereof. In other embodiments, the compositions, methods, kits and therapeutic combinations of the invention comprise (or employ the use of) enzalutamide and at least one alkylating agent. In a particular embodiment the alkylating agent is selected from the group consisting of carmustine, temozolomide, and derivatives and salts thereof. In other embodiments, the compositions, methods, kits and therapeutic combinations of the invention comprise (or employ the use of) enzalutamide and at least one anti-cancer agent selected from the group consisting of an alkylating agent and a RTK inhibitor, e.g. an EGFR antagonist. In other embodiments, the compositions, methods, kits and therapeutic combinations of the invention comprise (or employ the use of) enzalutamide, at least one alkylating agent selected from the group consisting of carmustine, temozolomide, and derivatives and salts thereof and at least one EGFR antagonist selected from the group consisting of afatinib, erlotinib and derivatives and salts thereof. Each possibility represents a separate embodiment of the invention.

In another embodiment the invention relates to a pharmaceutical composition for the treatment of brain tumors comprising: (i) enzalutamide, (ii) carmustine or temozolomide, (iii) erlotinib or afatinib, and (iv) one or more carriers, excipients or diluents. In a particular embodiment the composition is formulated for oral administration.

In another embodiment the invention relates to a kit comprising a combination of at least one AR antagonist or inhibitor such as enzalutamide, and at least one alkylating agent such as carmustine or temozolomide and at least one RTK inhibitor such as erlotinib or afatinib, further comprising instructions for administering said combination to a subject afflicted with an AR-expressing neuroepithelial tumor. In another embodiment, the kit comprises (i) enzalutamide, (ii) carmustine or temozolomide, (iii) erlotinib or afatinib and (iv) instructions for administering said combination to a subject afflicted with an AR-expressing neuroepithelial tumor. In a particular embodiment the neuroepithelial tumor is glioblastoma.

Therapeutic and Diagnostic Methods

In one aspect, the invention relates to enzalutamide or a derivative thereof for use in a method for the treatment of a neuroepithelial tumor (e.g. GBM) in a subject in need thereof, wherein the enzalutamide or derivative thereof is used in a therapeutically effective amount and the tumor is characterized by AR expression in at least a portion of the tumor cells. In another embodiment the invention provides a method for the treatment of a neuroepithelial tumor (e.g. GBM) characterized by AR expression in at least a portion of the tumor cells in a subject in need thereof, comprising administering to the subject a therapeutically effective amount of enzalutamide or a derivative thereof.

In another aspect, the invention relates to a method for the treatment of a glial tumor (e.g. GBM characterized by AR expression) in a subject in need thereof, comprising administering to the subject a therapeutically effective amount of at least one AR antagonist or inhibitor (e.g. enzalutamide). In another aspect, the invention relates to at least one AR antagonist or inhibitor (e.g. enzalutamide), for use in a method for the treatment of a glial tumor (e.g. GBM characterized by AR expression) in a subject in need thereof, the method comprising administering to the subject the at least one AR antagonist or inhibitor in a therapeutically effective amount.

In another aspect, there is provided a method of determining if a subject afflicted with a brain tumor (e.g. GBM) is amenable for treatment with an AR antagonist or inhibitor (e.g. enzalutamide), comprising determining the presence of at least one AR aberration selected from the group consisting of: amplification at the AR gene locus, LOH at the AR gene locus, AR over-expression and/or expression of at least one AR variant, in a sample of the subject, wherein the presence of the at least one aberration indicates that said subject is amenable for treatment with the AR antagonist or inhibitor. In another embodiment wherein said subject is determined to be amenable for treatment, the method further comprises administering said AR antagonist or inhibitor (e.g. enzalutamide), thereby treating said tumor in said subject.

In another embodiment the invention relates to an AR antagonist or inhibitor (e.g. enzalutamide) for use in tumor treatment in a subject afflicted with a brain tumor (e.g. GBM), wherein the subject has been determined to be amenable for treatment with the AR antagonist or inhibitor, by a method comprising determining the presence of at least one AR aberration selected from the group consisting of: amplification at the AR gene locus, LOH at the AR gene locus, AR over-expression and/or expression of at least one AR variant (e.g. at least one AR variant selected from the group consisting of an AR variant characterized by deletion or mutation at the LBD and a ligand-independent AR splice variant), in a sample of the subject, wherein the presence of the at least one aberration indicates that said subject is amenable for treatment with the AR antagonist or inhibitor. In another embodiment said AR antagonist or inhibitor is administered to said subject, thereby treating said tumor in said subject.

In another embodiment wherein expression of AR-V7 has been determined to be present in the sample, said AR antagonist or inhibitor (e.g. enzalutamide) is for use by administration to said subject in concurrent or sequential combination with at least one additional anti-cancer agent (e.g. an alkylating agent and/or a RTK inhibitor). In another embodiment the treatment comprises administering to said subject at least one AR antagonist or inhibitor (e.g. enzalutamide), at least one alkylating agent (e.g. temozolomide or carmustine) and at least one RTK inhibitor (e.g. afatinib or erlotinib).

A subject in need thereof, amenable for treatment according to embodiments of the invention, is a subject diagnosed with (or suspected of having) a brain tumor characterized by AR expression, or afflicted with a brain tumor (e.g. a neuroepithelial tumor such as GBM) as disclosed herein. An AR expressing tumor, also referred to herein as a tumor characterized by AR expression, denotes a tumor characterized by the presence of an AR polypeptide in at least a part of the tumor cells. A subject in need thereof may be identified according to various embodiments of the invention as amenable for treatment by compositions and methods of the invention, by determining the presence of at least one AR aberration as disclosed herein in a sample of the subject. Unless stated otherwise, the subject in need thereof referred to herein is a human subject. In one embodiment the subject is male. In another embodiment the subject is female.

Methods and means for determining the presence of aberrations to the AR gene or its expression have been described, and include a variety of molecular assays (e.g. amplification-based methods including, but not limited to polymerase chain reaction methods and hybridization-based methods, including, but not limited to Northern blotting and array analysis) and immunoassays (e.g. Western blotting or ELISA). Non limitative examples of such assays are described in the Examples section below. Reagents for implementing these methods are commercially available and may further be readily provided by the skilled artisan based on known sequences of the AR gene and products thereof.

For example, a human AR gene sequence may be as described in accession no. NC_000023.11, incorporated herein by reference. An AR transcript corresponding to wild-type (canonical) human AR and the corresponding AR protein may have sequences as described in accession no. NM 000044, incorporated herein by reference. AR variants (including those characterized by deletion or mutation at the LBD and ligand-independent AR splice variants e.g. AR-V7) are described, for example, in accession nos. ACZ81436.1, FJ235916 and NM_001348061.1, by Lu and Luo (2013) and in U.S. Pat. No. 8,841,422 and EP3062106, all incorporated herein by reference.

Exemplary amino acid sequences of the human gene products may be represented by the following:

```
MEVQLGLGRV YPRPPSKTYR GAFQNLFQSV REVIQNPGPR HPEAASAAPP GASLLLLQQQ

QQQQQQQQQQ QQQQQQQQQQ ETSPRQQQQQ QGEDGSPQAH RRGPTGYLVL DEEQQPSQPQ

SALECHPERG CVPEPGAAVA ASKGLPQQLP APPDEDDSAA PSTLSLLGPT FPGLSSCSAD

LKDILSEAST MQLLQQQQQE AVSEGSSSGR AREASGAPTS SKDNYLGGTS TISDNAKELC

KAVSVSMGLG VEALEHLSPG EQLRGDCMYA PLLGVPPAVR PTPCAPLAEC KGSLLDDSAG

KSTEDTAEYS PFKGGYTKGL EGESLGCSGS AAAGSSGTLE LPSTLSLYKS GALDEAAAYQ

SRDYYNFPLA LAGPPPPPPP PHPHARIKLE NPLDYGSAWA AAAAQCRYGD LASLHGAGAA

GPGSGSPSAA ASSSWHTLFT AEEGQLYGPC GGGGGGGGGG GGGGGGGGGG GGGEAGAVAP

YGYTRPPQGL AGQESDFTAP DVWYPGGMVS RVPYPSPTCV KSEMGPWMDS YSGPYGDMRL

ETARDHVLPI DYYFPPQKTC LICGDEASGC HYGALTCGSC KVFFKRAAEG KQKYLCASRN

DCTIDKFRRK NCPSCRLRKC YEAGMTLGAR KLKKLGNLKL QEEGEASSTT SPTEETTQKL

TVSHIEGYEC QPIFLNVLEA IEPGVVCAGH DNNQPDSFAA LLSSLNELGE RQLVHVVKWA

KALPGFRNLH VDDQMAVIQY SWMGLMVFAM GWRSFTNVNS RMLYFAPDLV FNEYRMHKSR

MYSQCVRMRH LSQEFGWLQI TPQEFLCMKA LLLFSIIPVD GLKNQKFFDE LRMNYIKELD

RIIACKRKNP TSCSRRFYQL TKLLDSVQPI ARELHQFTFD LLIKSHMVSV DFPEMMAEII

SVQVPKILSG KVKPIYFHTQ (SEQ ID NO: 1; wild-type AR, transcript
variant 1, NM_000044);
and

MEVQLGLGRV YPRPPSKTYR GAFQNLFQSV REVIQNPGPR HPEAASAAPP GASLLLLQQQ

QQQQQQQQQQ QQQQQQQQQQ ETSPRQQQQQ QGEDGSPQAH RRGPTGYLVL DEEQQPSQPQ

SALECHPERG CVPEPGAAVA ASKGLPQQLP APPDEDDSAA PSTLSLLGPT FPGLSSCSAD

LKDILSEAST MQLLQQQQQE AVSEGSSSGR AREASGAPTS SKDNYLGGTS TISDNAKELC

KAVSVSMGLG VEALEHLSPG EQLRGDCMYA PLLGVPPAVR PTPCAPLAEC KGSLLDDSAG

KSTEDTAEYS PFKGGYTKGL EGESLGCSGS AAAGSSGTLE LPSTLSLYKS GALDEAAAYQ

SRDYYNFPLA LAGPPPPPPP PHPHARIKLE NPLDYGSAWA AAAAQCRYGD LASLHGAGAA

GPGSGSPSAA ASSSWHTLFT AEEGQLYGPC GGGGGGGGGG GGGGGGGGGG GGGEAGAVAP

YGYTRPPQGL AGQESDFTAP DVWYPGGMVS RVPYPSPTCV KSEMGPWMDS YSGPYGDMRL

ETARDHVLPI DYYFPPQKTC LICGDEASGC HYGALTCGSC KVFFKRAAEG KQKYLCASRN

DCTIDKFRRK NCPSCRLRKC YEAGMTLGEK FRVGNCKHLK MTRP (SEQ ID NO 2;

AR-V7, transcript variant 3, NM_001348061.1).
```

A "sample of the subject" refers to a biological sample derived from the subject, which facilitates the determination of AR expression and/or aberrations as described herein. In some embodiments, the sample is obtained from a tissue or organ of interest. For example, biopsies from suspected tumors or lesions may be obtained by conventional methods. In other embodiments, the sample may be a fluid sample, e.g. blood, serum, plasma, tumor rinse fluids, urine and saliva samples. In some embodiments, the fluid sample is a cell-containing sample, e.g. a blood sample or tumor rinse sample. The sample may be processed (e.g. by centrifugation and/or filtration) to either enrich their relative content of cells, or to isolate the cell-free fraction. For example, blood samples are known to contain circulating tumor cells, released by primary tumor lesions into the blood. Cell containing samples (obtained from e.g. tissue biopsies or biological fluids) may be further processed by lysing and purification of protein and/or nucleic acids. In other embodiments, the use of cell-free blood samples is contemplated, from which circulating (cell-free) nucleic acids (e.g. DNA) released into the blood by apoptotic and necrotic tumor cells, may be isolated. In some embodiments, the sample is obtained in a non-invasive manner. For example, without limitation, urine samples and saliva samples may be used to detecting genetic aberrations. Methods for obtaining and processing biological samples are known to those of skill in the art.

The term "loss of heterozygosity" or "LOH" as used herein means the chromosomal condition wherein one of a pair of heterozygous alleles is lost due to a deletion of DNA from one of the paired chromosomes on which the allele is located, leaving only the remaining allele to be expressed and the affected cells functionally homozygous at the gene locus where the deletion occurred. LOH at the AR gene locus means that one copy of the AR allele pair has been lost. In some embodiments, the LOH is manifested by loss of the inactivated (e.g. methylated) AR allele. In other embodiments, the LOH is accompanied by amplification of the remaining allele.

The term "amplification" with respect to chromosomal aberrations refers to the presence of a higher than normal number of copies of a genomic nucleic acid sequence. It is understood by one of ordinary skill in the art that the presence of multiple copies of a gene within a genome may result in the production of a corresponding protein at elevated levels. Amplification at the AR gene locus means an increase in the number of copies of at least one AR allele in a cell compared to normal (non-tumor) cells.

The term "expression" refers to a gene that is transcribed or translated at a detectable level. As used herein, expression also encompasses "over-expression", which refers to a gene that is transcribed or translated at a detectably greater level, usually in a cancer cell, in comparison to a normal cell. As further described herein, the presence or detection of AR expression (including of variants thereof) in a sample denotes the presence of an AR polypeptide or transcript at a detectable level so as to determine that the subject from which the sample has been obtained is afflicted with an AR-expressing tumor. As further referred to herein, AR expression in a cell is associated with at least one AR biological function in the cell as described herein.

By means of a non-limiting example, methods of the invention may involve immunoassays such as Western blot or ELISA using antibodies directed to AR (optionally antibodies capable of differentiating between different AR splice variants), or assays based on dipstick technology or antibody array. In some embodiments, the methods of the invention are suitable for automated or semi-automated analysis, and may enable clinical, medium or high-throughput screening of multiple samples. For example, automated ELISA systems such as Biotest's QUICKSTEP® ELISA Processor, Maxmat Automated microwell ELISA analyzer (Maxmat S.A., France), or DSX™ Four-Plate System (Dynex Technologies) may conveniently be used. Other assays comprising AR detection by microscopy or cell ceytometry (e.g. fluorescence-activated cell sorting, FACS, using suitable antibodies as described above) may be employed. Such techniques are well known to the ordinarily skilled artisan and have been described in many standard immunology manuals and texts.

In addition, various amplification methods can also be used to determine whether the tumor or cell expresses AR or whether AR aberrations are present in the sample. Such methods include, without limitation, PCR, RT-PCR and in situ PCR (all the above referring also to "nested" PCR, and nested RT-PCR), LCR (ligase chain reaction) and 3SR (self sustained sequence replication). In accordance with a certain embodiments RT-PCR and nested RT-PCR are used. The amplification products are identified by methods used in the art such as by separation on a gel. Alternatively, if a sufficient quantity of the appropriate cells can be obtained, standard RNA analysis (e.g., Northern analysis, RNase protection, or primer extension) can be performed to determine the level of mRNA expression of the gene of interest. LOH and gene amplification may be measured using various techniques, including, but not limited to quantitative and semi quantitative PCR or RT-PCR, Southern blotting, high-resolution PCR based fluorescence quantitation using capillary electrophoresis systems, amplification of microsatellites by PCR using radiolabeled nucleotides followed by autoradiography and next generation sequencing (Ion Torrent™, Life Technologies).

In another embodiment, the diagnostic methods of the invention further comprise the step of administering a therapeutically effective amount of an AR antagonist or inhibitor (e.g. enzalutamide or a derivative thereof) to the subject exhibiting expression of AR or at least one aberration thereof in said sample (a subject determined to be amenable for treatment by a method as described herein).

In other embodiments, the methods of the invention further comprise determining whether the tumor is characterized by EGFR expression in at least a portion of the tumor cells. For example, when the presence of at least one aberration comprising expression of at least one AR variant selected from the group consisting of an AR variant characterized by deletion or mutation at the LBD and a ligand-independent AR splice variant (e.g. AR-V7) has been identified in at least a portion of the tumor cells and said tumor is further identified to be characterized by EGFR expression (including in some embodiments EGFR over-expression) in at least a portion of the tumor cells, the method may further comprise administering to said subject at least one AR antagonist or inhibitor (e.g. enzalutamide) in concurrent or sequential combination with at least one EGFR antagonist (e.g. afatinib and/or erlotinib), which may optionally ne administered in concurrent or sequential combination with at least one alkylating agent (e.g. temozolomide and/or carmustine).

In another aspect there is provided a kit for determining if a subject is amenable for treatment by an AR antagonist or inhibitor (e.g. enzalutamide or a derivative thereof), comprising means for determining the expression of AR or at least one aberration thereof in a sample of a subject. For example, without limitation, the kit may comprise one or more antibodies, PCR primers or other reagents that may be employed in various immunoassays and other molecular biology assays known in the art. Such reagents, e.g. antibodies, primers or probes, may be generated based on the reported sequences of AR, as described herein. In another embodiment, the kit may further comprise instructions for administering said antagonist or inhibitor to a subject determined to be amenable for treatment.

In some embodiments, the tumor is a neuroepithelial tumor. In other embodiments, said tumor is an astrocytoma. In other embodiments, said tumor is a glioma. In other embodiments, said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma. In other embodiments, said tumor is glioblastoma. In other embodiments, the tumor is meningioma.

In other embodiments, said tumor is characterized by amplification at the AR gene locus in at least a portion of the tumor cells. In other embodiments, the amplification is associated with AR gene copy number increase of 1-20. In other embodiments, the amplification is associated with AR gene copy number increase of 1-3, 1-5, 1-10, 1-20, 2-4, 2-6, 5-10 or 5-20. In other embodiments, said tumor is characterized by loss of heterozygosity (LOH) at the AR gene locus in at least a portion of the tumor cells. Thus, for example, the tumor may be characterized by AR copy number of 2-3, or in other embodiments, up to 5, resulting e.g. from amplification of one allele and LOH of the other allele, in at least a part of the tumor cells. In other embodiments, said tumor is characterized by loss of an inactivated AR allele (e.g. by methylation) in at least a portion of the tumor cells. In other embodiments, said tumor is characterized by AR over-expression in at least a portion of the tumor cells. In other embodiments, said over-expression is associated with 1.1-20 fold elevation of in the AR protein level. In other embodiments, said over-expression is associated with 1.1-150, 1.1-100, 1.1-50. 1.1-20, 1.1-10, 1.1-2, 1.2-3, 1.3-4, 1.2-1.6, 1.4-5 1.2-20 or 1.3-10 fold elevation of in the AR protein level. In other embodiments, said over-expression is associated with 1.1-350,000, 2-3,500, 2.5-350, 3-100, 1.1-35, 1.1-20, 2-20, 2-10 or 1.1-10 fold elevation of in the AR mRNA level.

In other embodiments, said tumor is characterized by expression of at least one AR variant in at least a portion of the tumor cells, wherein the variant is selected from the group consisting of a variant characterized by deletion or mutation at the ligand binding domain (LBD) and a ligand-independent AR splice variant. In other embodiments, said variant is AR variant 7 (AR-V7). In other embodiments, aid tumor is characterized by over-expression of wild-type AR and by expression of AR-V7 in at least a portion of the tumor cells. In other embodiments, said tumor is characterized by over-expression of wild-type AR and AR-V7 in at least a portion of the tumor cells. In other embodiments, said tumor is characterized by expression of AR-V7 and is further characterized by LOH at the AR gene locus, in at least a portion of the tumor cells.

In other embodiments, the presence of at least one, two, three, four or five AR aberrations selected from the group consisting of: amplification at the AR gene locus, LOH at the AR gene locus, AR over-expression and/or expression of at least one AR variant, in a sample of a subject, indicates that the subject is amenable for treatment by the compositions, methods and kits of the invention. In other embodiments, the presence of at least one, two, three, four or five AR aberrations as described herein in a sample of a subject indicates that the subject is amenable for treatment by the compositions, methods and kits of the invention. In other embodiments, the sample is a brain tumor biopsy. In other embodiments, the sample is a blood sample. In other embodiments, said sample is a cell-free blood sample. In other embodiments, if said subject is determined to be amenable for treatment, methods according to the invention may further comprise a step of administering an AR antagonist or inhibitor or in other embodiments a composition or combination of the invention to said subject, thereby treating said tumor in said subject.

In another embodiment the subject is human. In another embodiment, the subject is female. In another embodiment the subject is male. In another embodiment, said subject is not concomitantly afflicted with a tumor of non-neurological origin, e.g. prostate cancer or breast cancer.

In other embodiments, the subject is under treatment with at least one additional anti-cancer agent. In other embodiments, the AR antagonist or inhibitor is administered in concurrent or sequential combination with at least one additional anti-cancer agent. In other embodiments, the invention relates to a composition or kit comprising an AR antagonist or inhibitor in combination with at least one additional anti-cancer agent, useful in employing the methods of the invention.

In other embodiments, the at least one additional anti-cancer agent is selected from the group consisting of a chemotherapeutic drug, a RTK inhibitor, an immunotherapy and an anti-angiogenic therapy. In other embodiments, the at least one additional anti-cancer agent comprises radiotherapy. In other embodiments, the at least one additional anti-cancer agent comprises a chemotherapeutic drug. In other embodiments, the chemotherapeutic drug is an alkylating agent. In other embodiments, the alkylating agent is selected from the group consisting of temozolomide, carmustine and derivatives and salts thereof. In other embodiments, the at least one anti-cancer agent comprises a RTK inhibitor. In other embodiments, the RTK inhibitor is an EGFR antagonist. In other embodiments, the EGFR antagonist is selected from the group consisting of afatinib, erlotinib and derivatives and salts thereof. In other embodiments, said at least one anti-cancer agent comprises at least one alkylating agent and at least one EGFR antagonist. In other embodiments, the AR antagonist or inhibitor is enzalutamide or a derivative thereof. In other embodiments, the AR antagonist or inhibitor is enzalutamide. In other embodiments, the composition comprises enzalutamide, carmustine and erlotinib. In other embodiments, the composition comprises enzalutamide, carmustine and afatinib. In other embodiments, the methods of the invention comprise administering to the subject enzalutamide, carmustine and erlotinib. In other embodiments, the methods of the invention comprise administering to the subject enzalutamide, carmustine and afatinib.

For example, without limitation, a treatment schedule for a subject in need thereof afflicted with an AR-expressing GBM may include treatment by irradiation followed by temozolomide treatment (e.g. 150-200 mg/m 2/day PO) on days 1-5 every 28 days, for six to eight cycles. Enzalutamide may be administered according to some embodiments in sequential combination with the adjunct therapy, e.g. on days 6-28 each cycle.

As used herein, a therapeutically effective amount means an amount of a compound effective to prevent, alleviate or ameliorate symptoms of a disease of the subject being treated, such as cancer. Accordingly, a therapeutically effective amount for use in embodiments of the invention is an amount sufficient to inhibit tumor development or tumor cell survival under the conditions used. Determination of a therapeutically effective amount is well within the capability of those skilled in the art, especially in light of the detailed disclosure and Examples provided herein. In some embodiments, enzalutamide may be used at daily doses of e.g. 160-600 mg. In other embodiments, the combinations of the invention employ the use of doses (e.g. of the AR antagonist or inhibitor, alkylating agent and/or RTK inhibitor) that are at least 5%, 10%, 20%, 30%, 40%, 50%, 60%, 70%, 80% or 90% lower than those commonly used for human therapy. Accordingly, a therapeutically effective amount of enzalutamide for oral administration to human subjects, when used as a sole active ingredient, may be e.g. 160-600, 200-500, 200-400, or 300-600 mg/day. A therapeutically effective amount of enzalutamide for oral administration to human subjects, when used in combination with at least one anti-cancer agent, may be e.g. 150-570, 140-540, 130-480, 110-420 or 100-360 mg/day. For local, topical or intratumoral administration, a therapeutically effective amount may be e.g. 20-160, 20-100 or 20-80 µM. As exemplified herein, enzalutamide concentrations of at least 20 µM are more effective in embodiments of the invention than lower concentrations such as 10 µM.

Additional exemplary embodiments of compositions, methods and kits according to the invention are described hereinbelow.

Additional Embodiments

1. A pharmaceutical composition for the treatment of brain tumors, comprising at least one androgen receptor (AR) antagonist or inhibitor and at least one anti-cancer agent selected from the group consisting of an alkylating agent and a receptor tyrosine kinase (RTK) inhibitor.

2. The composition of clause 1, comprising at least one AR antagonist or inhibitor, at least one alkylating agent and at least one RTK inhibitor.

3. The composition of clause 1 or 2, wherein the AR antagonist or inhibitor is enzalutamide or a derivative thereof.

4. The composition according to any one of the preceding clauses, wherein the alkylating agent is selected from the group consisting of temozolomide, carmustine and derivatives and salts thereof.

5. The composition according to any one of the preceding clauses, wherein the RTK inhibitor is selected from the group consisting of afatinib, erlotinib, and derivatives and salts thereof.

6. The composition of clause 2, comprising enzalutamide, carmustine and erlotinib or afatinib.

7. The composition according to any one of the preceding clauses, further comprising one or more carriers, excipients or diluents.

8. The composition of clause 7, formulated for oral administration.

9. A kit comprising a combination of at least one AR antagonist or inhibitor and at least one anti-cancer agent selected from the group consisting of an alkylating agent and a RTK inhibitor, further comprising instructions for administering said combination to a subject afflicted with an AR-expressing neuroepithelial tumor.

10. The kit of clause 9, wherein the neuroepithelial tumor is glioblastoma.

11. A method of treating a brain tumor characterized by AR expression in at least a portion of the tumor cells in a subject in need thereof, comprising administering to the subject a therapeutic combination of at least one AR antagonist or inhibitor and at least one anti-cancer agent selected from the group consisting of an alkylating agent and a RTK inhibitor.

12. The method of clause 11, wherein the therapeutic combination is in the form of a pharmaceutical composition according to any one of clauses 1-8.

13. The method of clause 11, wherein the tumor is a neuroepithelial tumor.

14. The method of clause 13, wherein said tumor is an astrocytoma.

15. The method of clause 14, wherein said tumor is a glioma.

16. The method of clause 14, wherein said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma.

17. The method of clause 14, wherein said tumor is glioblastoma.

18. The method of clause 11, wherein the tumor is meningioma.

19. The method according to any one of the preceding clauses, wherein said tumor is characterized by amplification at the AR gene locus in at least a portion of the tumor cells.

20. The method of clause 19, wherein the amplification is associated with AR gene copy number increase of 1-20.

21. The method of any one of the preceding clauses, wherein said tumor is characterized by loss of heterozygosity (LOH) at the AR gene locus in at least a portion of the tumor cells.

22. The method of any one of the preceding clauses, wherein said tumor is characterized by AR over-expression in at least a portion of the tumor cells.

23. The method of clause 22, wherein said over-expression is associated with 1.1-20 fold elevation of in the AR protein level.

24. The method of clause 11 wherein said tumor is characterized by expression of at least one AR variant in at least a portion of the tumor cells, wherein the variant is selected from the group consisting of a variant characterized by deletion or mutation at the ligand binding domain (LBD) and a ligand-independent AR splice variant.

25. The method of clause 24 wherein said variant is AR variant 7 (AR-V7).

26. The method of clause 25 wherein said tumor is characterized by over-expression of wild-type AR and by expression of AR-V7 in at least a portion of the tumor cells.

27. The method of clause 25 wherein said tumor is characterized by over-expression of wild-type AR and AR-V7 in at least a portion of the tumor cells.

28. The method of clause 25 wherein said tumor is characterized by expression of AR-V7 and is further characterized by LOH at the AR gene locus, in at least a portion of the tumor cells.

29. The method according to any one of the preceding clauses, wherein the subject is human.

30. The method according to any one of the preceding clauses wherein the subject is female.

31. A method for the treatment of a glial tumor in a subject in need thereof, comprising administering to the subject a therapeutically effective amount of at least one AR antagonist or inhibitor.

32. A method for the treatment of a neuroepithelial tumor characterized by AR expression in at least a portion of the tumor cells in a subject in need thereof, comprising administering to the subject a therapeutically effective amount of enzalutamide or a derivative thereof.

33. The method of clause 31 or 32, wherein said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma.

34. The method of clause 33, wherein said tumor is glioblastoma.

35. The method according to any one of clauses 31-34, wherein said tumor is characterized by: amplification at the AR gene locus, LOH at the AR gene locus, AR over-expression and/or expression of at least one AR variant, in at least a portion of the tumor cells.

36. The method of clause 35, wherein the amplification is associated with AR gene copy number increase of 1-20.

37. The method of clause 35, wherein said over-expression is associated with elevation of 1.1-20 fold in the AR protein level.

38. The method of clause 35 wherein the variant is selected from the group consisting of a variant characterized by deletion or mutation at the ligand binding domain (LBD) and a ligand-independent AR splice variant.

39. The method of clause 38 wherein said variant is AR variant 7 (AR-V7).

40. The method of clause 39 wherein said tumor is further characterized by at least one of: over-expression of wild-type AR, over-expression of AR-V7, and LOH at the AR gene locus, in at least a portion of the tumor cells.

41. The method of any one of clauses 31-40, wherein the subject is human.

42. The method of any one of clauses 31-41 wherein the subject is female.

43. The method of any one of clauses 31-42 comprising administering to the subject enzalutamide, thereby treating said tumor.

44. The method of any one of clauses 31-43, wherein the subject is under treatment with at least one additional anti-cancer agent.

45. The method of clause 44 wherein the at least one additional anti-cancer agent is selected from the group consisting of a chemotherapeutic drug, a RTK inhibitor, an immunotherapy and an anti-angiogenic therapy.

46. The method of clause 44, wherein the at least one additional anti-cancer agent comprises radiotherapy.

47. The method of clause 44 wherein the at least one additional anti-cancer agent comprises a chemotherapeutic drug.

48. The method of clause 46 wherein the chemotherapeutic drug is an alkylating agent.

49. The method of clause 47 wherein the alkylating agent is selected from the group consisting of temozolomide, carmustine and derivatives and salts thereof.

50. The method of clause 44 wherein the at least one anti-cancer agent comprises a RTK inhibitor.

51. The method of clause 50 wherein the RTK inhibitor is an EGFR antagonist.

52. The method of clause 51 wherein the EGFR antagonist is selected from the group consisting of afatinib, erlotinib and derivatives and salts thereof.

53. The method of clause 44 wherein said at least one anti-cancer agent comprises at least one alkylating agent and at least one EGFR antagonist.

54. A method of determining if a subject afflicted with a brain tumor is amenable for treatment with an AR antagonist or inhibitor, comprising determining the presence of at least one AR aberration selected from the group consisting of: amplification at the AR gene locus, LOH at the AR gene locus, AR over-expression and/or expression of at least one AR variant, in a sample of the subject, wherein the presence of the at least one aberration indicates that said subject is amenable for treatment with the AR antagonist or inhibitor.

55. The method of clause 54, wherein the at least one aberration comprises expression of at least one AR variant selected from the group consisting of an AR variant characterized by deletion or mutation at the LBD and a ligand-independent AR splice variant.

56. The method of clause 55, wherein said variant is AR-V7.

57. The method of any one of clause 54-56, wherein the presence of at least two aberrations indicates that said subject is amenable for treatment.

58. The method of any one of clause 54-56, wherein the presence of at least three aberrations indicates that said subject is amenable for treatment.

59. The method of any one of clauses 54-58 wherein the at least one aberration comprises amplification at the AR gene locus.

60. The method of clause 59 wherein the amplification is associated with AR gene copy number increase of 1-20.

61. The method of any one of clauses 54-60, wherein said over-expression is associated with elevation of 1.1-20 fold in the AR protein level.

62. The method of any one of clauses 54-61, wherein the sample is a brain tumor biopsy.

63. The method of any one of clauses 54-61 wherein the sample is a blood sample.

64. The method of clause 63, wherein said sample is a cell-free blood sample.

65. The method of any one of clauses 54-64, wherein the tumor is a neuroepithelial tumor.

66. The method of clause 65, wherein said tumor is an astrocytoma.

67. The method of clause 66, wherein said tumor is a glioma.

68. The method of clause 66, wherein said tumor is selected from the group consisting of glioblastoma, anaplastic astrocytoma, diffuse astrocytoma, oligodendroglioma, anaplastic oligodendroglioma, oligoasrocytoma and anaplastic oligoastrocytoma.

69. The method of clause 68, wherein said tumor is glioblastoma.

70. The method of any one of clauses 54-64, wherein the tumor is meningioma.

71. The method of any one of clauses 54-70, wherein the subject is human.

72. The method of any one of clauses 54-71 wherein the subject is female.

73. The method of any one of clauses 54-72, wherein if said subject is determined to be amenable for treatment, the method further comprises administering said AR antagonist or inhibitor, thereby treating said tumor in said subject.

74. The method of any one of clauses 54-73, wherein the AR antagonist or inhibitor is enzalutamide or a derivative thereof.

75. The method of clause 74, wherein said AR antagonist or inhibitor is enzalutamide.

76. The method of any one of clauses 54-75, wherein said AR antagonist or inhibitor is administered in concurrent or sequential combination with at least one additional anti-cancer agent.

77. The method of clause 76 wherein the at least one anti-cancer agent is selected from the group consisting of an alkylating agent and a RTK inhibitor.

78. The method of clause 77 wherein said at least one anti-cancer agent is selected from the group consisting of temozolomide, carmustine, afatinib, erlotinib, and derivatives and salts thereof.

79. The method of clause 76 comprising administering to said subject at least one AR antagonist or inhibitor, at least one alkylating agent and at least one RTK inhibitor.

80. The method of clause 79 comprising administering to said subject enzalutamide, carmustine and erlotinib.

81. The method of clause 55 or 56, comprising administering to the subject determined to be amenable for treatment at least one AR antagonist or inhibitor in concurrent or sequential combination with at least one additional anti-cancer agent.

82. The method of clause 81, further comprising determining whether the tumor is characterized by EGFR expression in at least a portion of the tumor cells, wherein if said tumor is further characterized by EGFR expression in at least a portion of the tumor cells, the method further comprises administering to said subject at least one AR antagonist or inhibitor in concurrent or sequential combination with at least one EGFR antagonist.

83. The method of clause 82, comprising administering to said subject enzalutamide in concurrent or sequential combination with at least one EGFR antagonist selected from the group consisting of afatinib, erlotinib and derivatives and salts thereof.

The following examples are presented in order to more fully illustrate some embodiments of the invention. They should, in no way be construed, however, as limiting the broad scope of the invention.

EXAMPLES

Methods
Patients and Tumors

DNA study was performed on paraffin embedded GBM tumors from 35 women. The study was approved by the local institutional research ethics committee, and all patients signed written consent forms.

Expression study was done on 30 GBM tumors from women and men patients who underwent surgery for primary supratentorial glioblastoma. The study group included patients with newly diagnosed glioblastoma, aged 18 to 75. Exclusion criteria included previous diagnosis of low-grade glioma, and patients with tumors positive for IDH1 mutation. The participating patients granted written informed consent according to an institutional review board-approved protocol.

DNA Extraction

DNA was extracted from formalin-fixed, paraffin-embedded GBM samples section using QIAamp DNA (FFPE Tissue Kit QIAGEN) according to the manufacturer's instructions. DNA Samples were quantified using a dsDNA-binding fluorescent dye (PICOGREEN® assay, Cat. No. P11496, Life Technologies, USA).

DNA was extracted from 200-μl aliquots of whole blood by Blood-DNA Mini Kit (Qiagen, Hildan, Germany) according to the manufacturer's instructions.

OncoScan Analysis

To obtain genome-wide copy number and loss-of-heterozygosity (LOH) profiles from FFPE tumor samples, 80 ng of FFPE-derived DNA was subjected to OncoScan FFPE Express 2.0 Affymetrix array (Affymetrix Inc., Santa Clara, Calif., USA). The assay was done according to manufacturer instructions. The data was analyzed using the Nexus 6 Copy Number™ software (Biodiscovery, CA).

Chromosome X-Inactivation Studies:

The MspI/HpaII pair of isoschizomeric enzymes (New England Biolabs, Beverly, Mass., USA) was used to analyze DNA methylation status at the AR locus. Whereas MspI cleaves the recognition sequence 5'-CCGG independently of the methylation state of the internal C, the restriction by HpaII is blocked by the presence of 5-MeC at this site. DNA samples (0.2 μg) were incubated for 2 Hr at 37° C. with 20 units of HpaII or MspI (Life Technologies, Inc.) in a 20 μl reaction volume. The same amount of each DNA was incubated without enzyme in a sham reaction. Blood DNA was used as a control for the HpaII restriction. The restriction enzymes were inactivated at 95° C. for 10 min. This step was followed by 40 cycles of a real-time PCR reaction with primers flanking the CCGG restriction sites in AR gene: AR-F: TGCGCGAAGTGATCCAGAA and AR-R: TCTGGGACGCAACCTCTCTC-3', SEQ ID NOs: 3 and 4, respectively); GAPDH was used as a control GAPDH-F: GTATTGGGCGCCTGGTCA; GAPDH-R: AGGGGTCAT-TGATGGCAACA (SEQ ID NOs: 5 and 6, respectively) at an annealing temperature of 60° C. (15 s). Performing the sham reaction allowed the determination of methylation status by comparing the quantification cycles with and without the HpaII digestion. Melting curve analysis was performed to verify the specificity of the PCR product.

RNA Extraction, cDNA Preparation qPCR
RNA Isolation

Total RNA was isolated from snap frozen gliomas or cell cultures using TRI Reagent according to the manufacturer's instructions (Sigma-Aldrich). The control RNAs were taken from a commercial mix of total RNA pooled from brain samples of 23 donors (mean age 68 years; 13 males and 10 females—FIRSTCHOICE® Human Brain Reference Total RNA, Ambion Inc., Cat. No. 6050) cDNA cDNA was produced from 0.2 ug of total RNA using the qScript microRNA cDNA Synthesis Kit (Quanta Biosciences), according to the manufacturer's instructions.

Real-Time Polymerase Chain Reaction Amplification and Relative Quantification

AR RNA expression was analyzed by StepOne real time RT PCR (Life Technologies). The reaction mixture included 1 μl of cDNA, 300 nmol/l concentrations of the following primers (Syntezza, Israel): AR-F: ACCGAG-GAGCTTTCCAGAATC, AR-R: AGGCTCTGGGACGCAACCT (SEQ ID NOs: 7 and 8, respectively); HPRT-F: GATGGTCAAGGTCGCAAGC; HPRT-R: ATATCCTACAACAAACTTGTCTGGAA (SEQ ID NOs: 9 and 10, respectively) and 5 μl of SYBR green mix (Perfecta Syber Green Fast Mix ROX, Quanta Biosciences) in a total volume of 10 μl according to manufacture instructions. The fold changes of AR mRNAs were normalized to HPRT. Following normalization, the fold changes of each mRNA were calculated based on the ratio between the analyzed tumor/cell line sample and normal brain or HEK 293 as indicated. The experiment was repeated three times in triplicate and the results are presented as the mean±SD. Statistical significance of induction of gene expression as compared to control was calculated using 2-tailed t test.

mRNA Expression of Androgen Receptor Splice Variants

AR variant 7 (A3) was analyzed by qPCR as described above using the following primers pair: AR-7-F: CCATCTTGTCGTCTTCGGAAATGTTATGAAGC AR-7-R: TTTGAATGAGGCAAGTCAGCCTTTCT (SEQ ID NOs: 11 and 12, respectively). The resulting 125 bp fragments were also electrophoresed on 3.5% metaphor and visualized by Ethidium bromide staining. Variant 5, 6 was amplified by PCR and the resulting 888 and 968 bp fragments were analyzed on 1.5% agarose gel.

Western Blot Analysis

For Western blotting analyses, tissue samples or cell lines pellets were homogenized in 500 ul of RIPA buffer supplemented with protease inhibitors (Thermo Fisher Scientific Inc). Protein concentration was determined using the Bradford protein assay (Bio-Rad, Richmond, Calif.). Tissue/cell line lysates containing 100 ug protein were separated by 4%-20% Tris-Glycine SDS-PAGE gels (Thermo Fisher Scientific) and assessed by western blot analysis, using sequential probing with either polyclonal antibody against AR (N20, 1:200 dilution); monoclonal anti-GAPDH (0411, diluted 1:10000) (Santa Cruz Biotechnologies, Santa Cruz, Calif. USA,) or Anti-β-Actin (AC-74 diluted 1:5000) Sigma as indicated and with the relevant secondary horseradish peroxidase-conjugated antibody (Santa Cruz Biotechnologies).

Cell Culture

The cell lines A172, U87MG and T98G (Glioblastoma), were obtained from the American Type Culture Collection (VA, USA). A172 and U87MG cells were cultured in DMEM-Eagle medium supplemented with 4 mmol/L L-glutamine, 100 units/ml penicillin and 100 µg/ml streptomycin, and 10% FBS Charcoal Stripped (Biological Industries, Israel). The T98G cells were cultured in Eagle's minimum essential medium supplemented with 4 mmol/L L-glutamine, 100 units/ml penicillin and 100 µg/ml streptomycin. To avoid the influence of FBS derived steroid hormone on AR, the cell media were supplemented with 10% charcoal/dextran-treated (stripped) FBS (Biological Industries). The cells were maintained in a humidified incubator at 37° C. in 5% $CO_2$.

Treatment with AR and EGFR Inhibitors $1\times10^3$ cells were plated in triplicate in 24-well plates, and allowed to attach overnight. The growth medium was replaced with medium containing 10 µM DHT (Sigma-Aldrich), and the indicated concentrations of AR inhibitors, enzalutamide (A2S technologies) or bicalutamide (Sigma-Aldrich), the alkylating agent 1,3-bis(2-chloroethyl)-1-nitrosourea (BCNU) (Sigma-Aldrich) and the EGFR inhibitors, erlotinib (TARCEVA®, F. Hoffmann-La Roche Ltd), Cetuximab (ERBITUX®) (Merck KGaA) and afatinib (A2S technologies) for 48 h and 72 h. The DHT concentration was chosen because it had no effect on cell viability in any of the cell lines as compared to cells treated with vehicle (0.15% ETOH).

Cell Survival

Crystal violet dye binding assay was used to measure cell viability as follows. 0.5% Crystal violet (Sigma-Aldrich MO, USA), was added to each cell well following fixation with 4% Paraformaldehyde (Gadot, Israel) the dye was solubilized with 10% acetic acid (Gadot) and read at 590 nm in a DTX 880 multimodes detectors microplate reader (Beckman Coulter, Switzerland). The average absorbance value of control was considered as 100% and the treated sample percentages were calculated by comparing the average absorbance of treated samples with the average absorbance of the control.

Cell Cycle Analysis

A172 glioma cell lines were treated with vehicle (0.15% ETOH), 10 µm of DHT with or without 40 or 80 µM Enzalutamide for 48 hr as indicated above. Then, the cells were harvested with trypsin and washed in PBS. This was followed by fixation for overnight at 0° C. in cold 80% Ethanol. After washing the cells in PBS and treatment with 50 µl of a 100 µg/ml RNase, 200 µl of Propidium iodide (PI) (from 50 µg/ml stock solution) was added. Propidium iodide fluorescence intensity was measured by flow cytometry using FL2 and 488 nM laser excitation.

Abbreviations

Throughout the specification and drawings, ENZ indicates enzalutamide, BIC indicates bicalutamide, U87 indicates U87MG cells, uM indicates micromolar (µM), GAPDH indicates Glyceraldehyde-3-Phosphate Dehydrogenase, DHT indicates Dihydrotestosterone, Afa, indicates afatinib, and Tra indicates erlotinib (TARCEVA®).

Example 1. Amplification of AR DNA Locus Accompanied with Loss of Heterozygosity (LOH)

To elucidate unknown genetic changes in GBM that might lead to identification of new treatment candidates, a genome-wide copy number and loss of heterozygosity array (OncoScan FFPE Express, Affymetrix) was performed on DNA extracted from 5 formalin fixed paraffin embedded GBM samples of 5 women. In Addition to the known genetic aberrations, amplification of Androgen receptor (AR) region (Xq12) was revealed in 4 of the 5 samples; in three of these samples, amplification was accompanied by loss of heterozygosity (LOH) in the remaining allele. In one sample there was no change in the AR region.

Example 2. Chromosome Inactivation Studies

Chromosome inactivation studies based on the differential methylation patterns of active and inactive alleles done on GBM samples from 35 women, revealed that the inactivated allele of this region was lost in 34 samples (FIG. 1). In the experiments described in FIG. 1, DNA samples (0.2 µg) were incubated for 2 Hr at 37° C. with 20 units of HpaII or MspI in a 20 µl reaction volume. The same amount of each DNA was incubated without enzyme in a sham reaction. Blood DNA was used as a control, as well as GBM and blood samples obtained from male subjects (indicated "man tumor" and "man blood", respectively). This step was followed by 40 cycles of a real-time PCR reaction with primers flanking the CCGG restriction sites in AR gene. AR amplification is demonstrated as melt curve of the amplified amplicon. The amplification of the uncut DNA is compared to those restricted with HpaII/MspI as indicated in the graph.

Samples

Focal copy-number-variation (CNV) analysis for AR chromosomal region done by droplet-digital-PCR, demonstrated AR amplification in 27% of GBM of males (n=22) and in females (n=21), the remaining active allele was at least duplicated in 62% (Table 1).

TABLE 1

| AR CNV in GBM. | | | | | |
|---|---|---|---|---|---|
| Men (n = 22) | | | Women (n = 21) | | |
| AR Copy number | No. | % | AR Copy number | No. | % |
| 1 | 16 | 72.7% | 1 | 6 | 27.3% |
| 2 | 5 | 22.73% | 2 | 7 | 31.82% |
| 3 | 1 | 4.55% | 3 | 8 | 36.36% |

Example 3. AR Expression in Gliomas

Figure 2A:
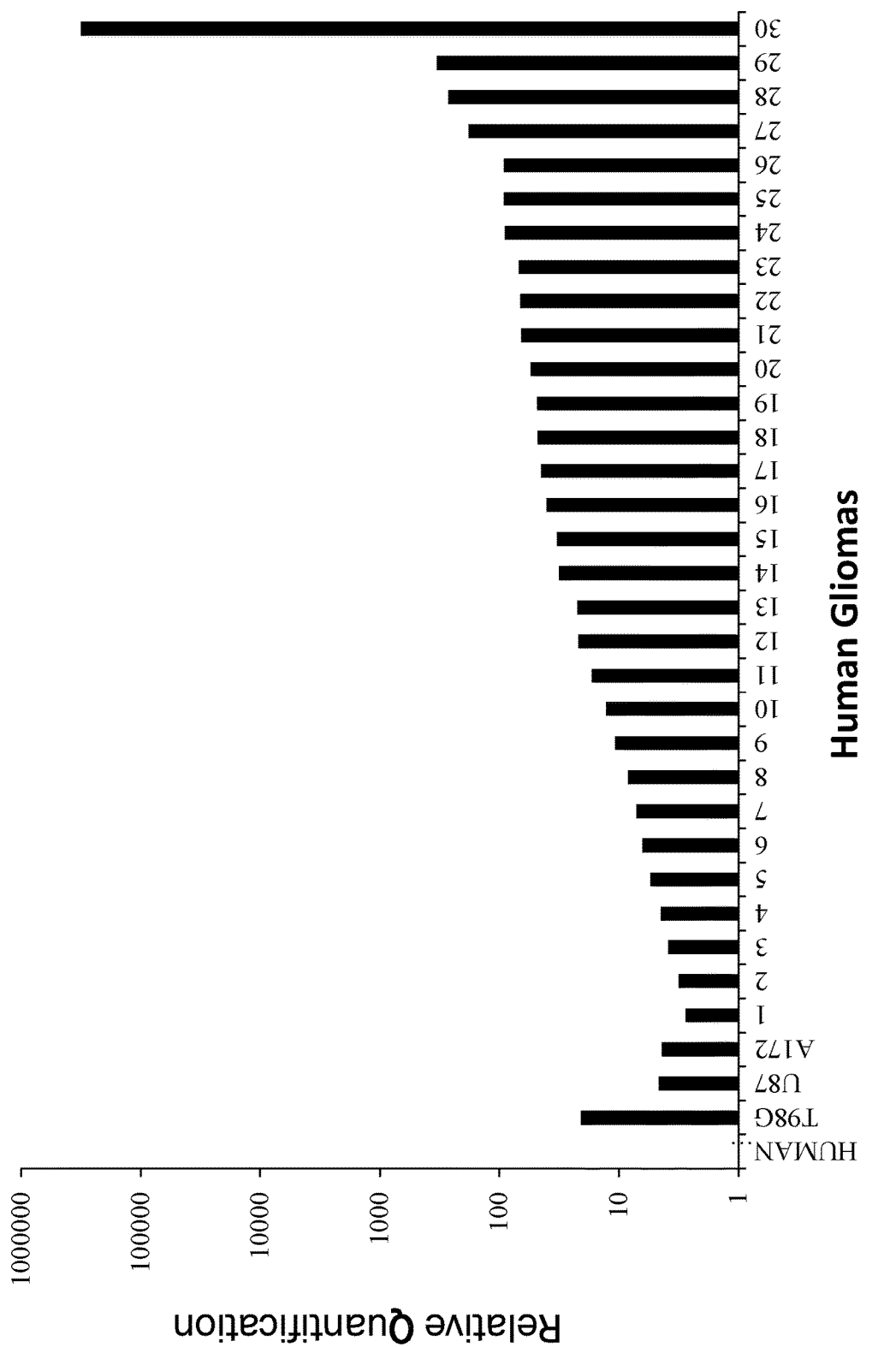
FIGS. 2A-2G. AR RNA expression in tumors compared to normal tissue.
Figure 3:
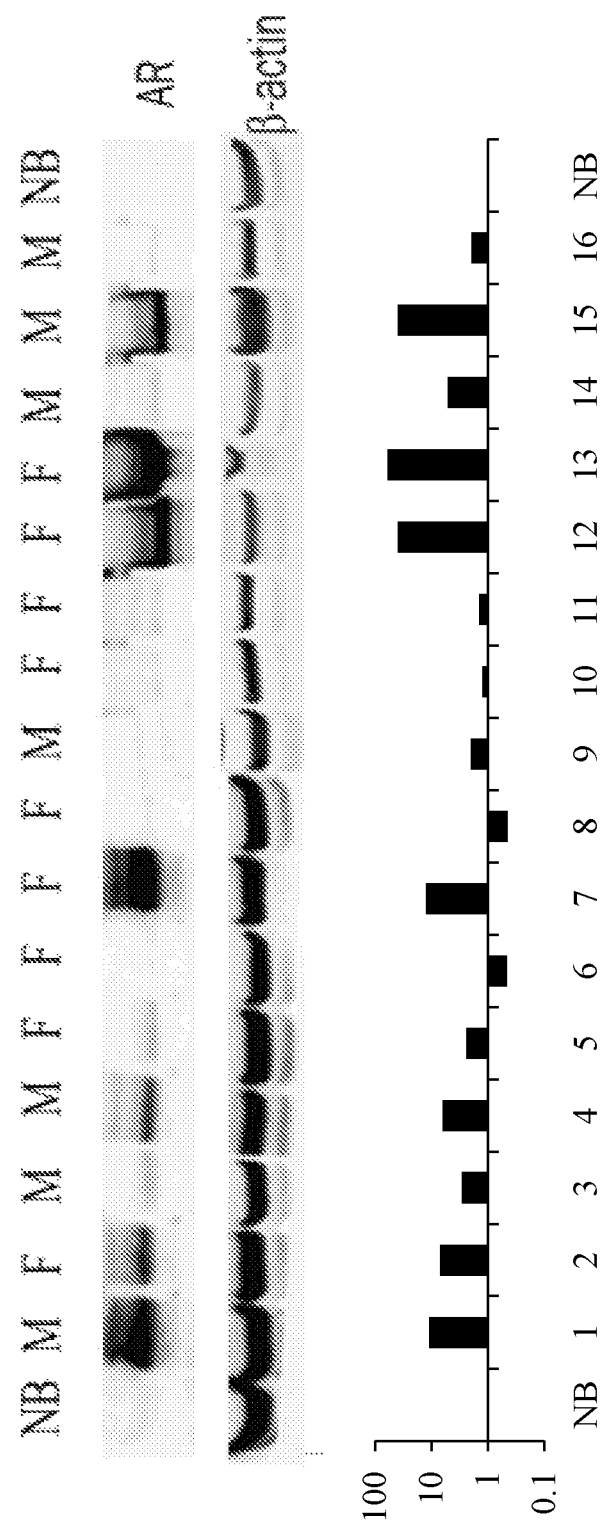
FIG. 3. AR protein expression in GBM. Western blot analysis, using sequential probing with either polyclonal antibody against AR (N20) upper lanes; or Anti-β-Actin (AC-74) lower lanes, on 16 female (F) or male (M) GBM samples and 1 normal brain (NB). Histograms depict the relative intensities quantified.

Quantitative real-time RT PCR (qPCR) and western blot analysis on RNA and protein (N=30 and 16, respectively)

extracted from GBM specimens of men and women demonstrated a significant induction of AR RNA expression (2.76-315,984 induction fold) (FIG. 2A) and of AR protein expression (1.7-106 induction fold) (FIG. 3) in 93% and 87% respectively compared to non-tumor cells regardless of patient's sex (t-test; RNA analysis, p=0.37; protein analysis, p=0.691). FIG. 2A depicts Quantitative PCR (qPCR) analysis of AR mRNA expression following normalization to HPRT in 30 GBM tumor samples and 3 GBM cell lines (T98G, U87 and A172). A commercial RNA mixture of 23 normal brains ("HUMAN") was used as a negative control.

Figure 2B:
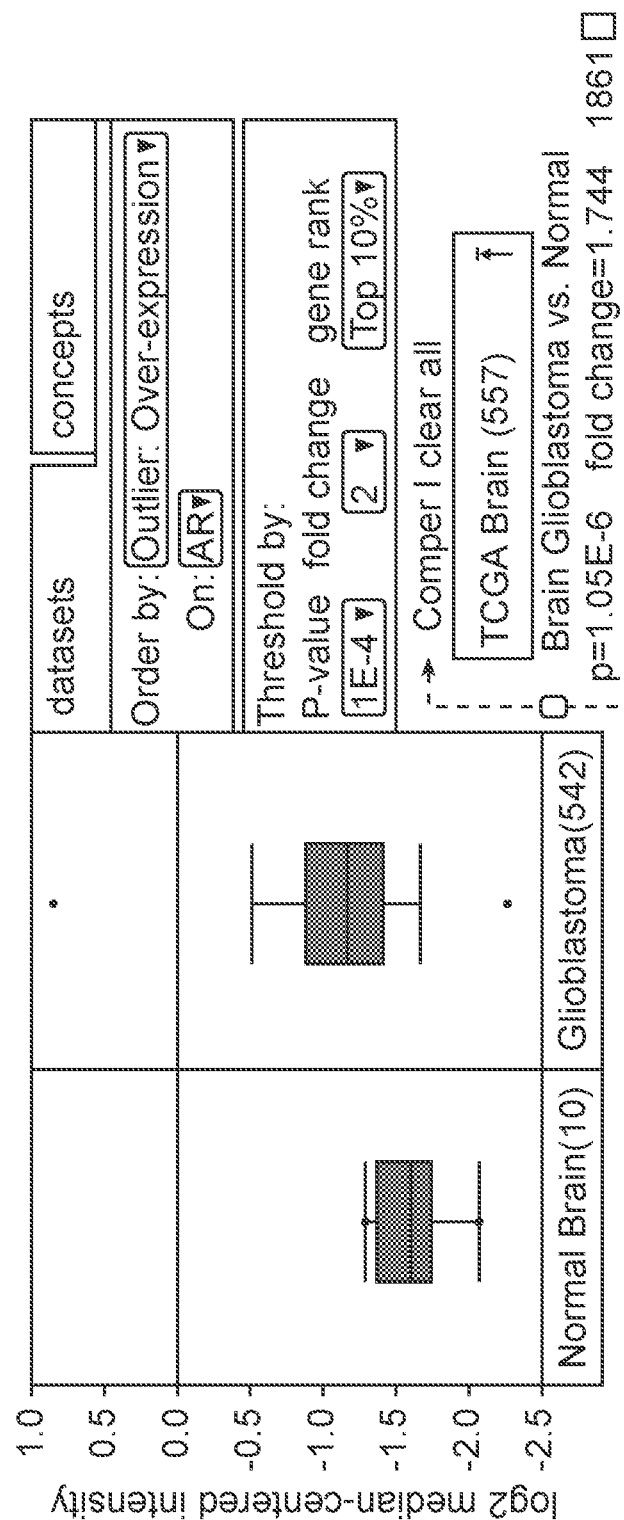
Figure 2C:
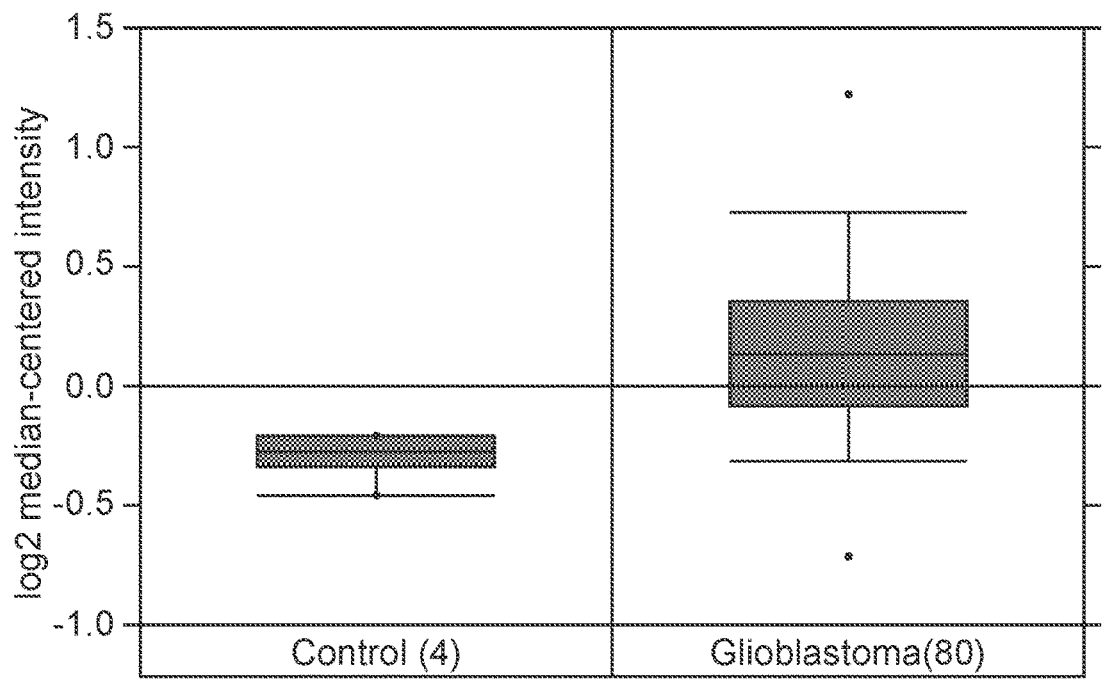
Figure 2D:
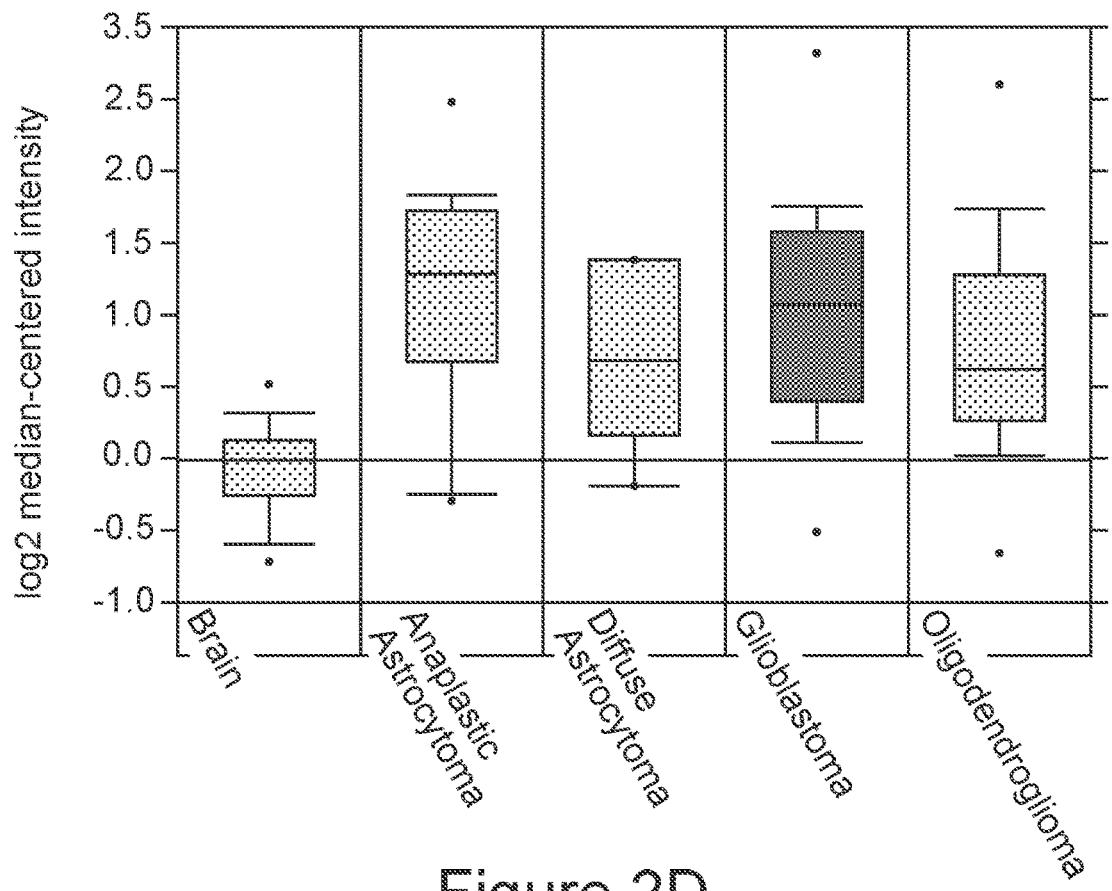
Figure 2E:
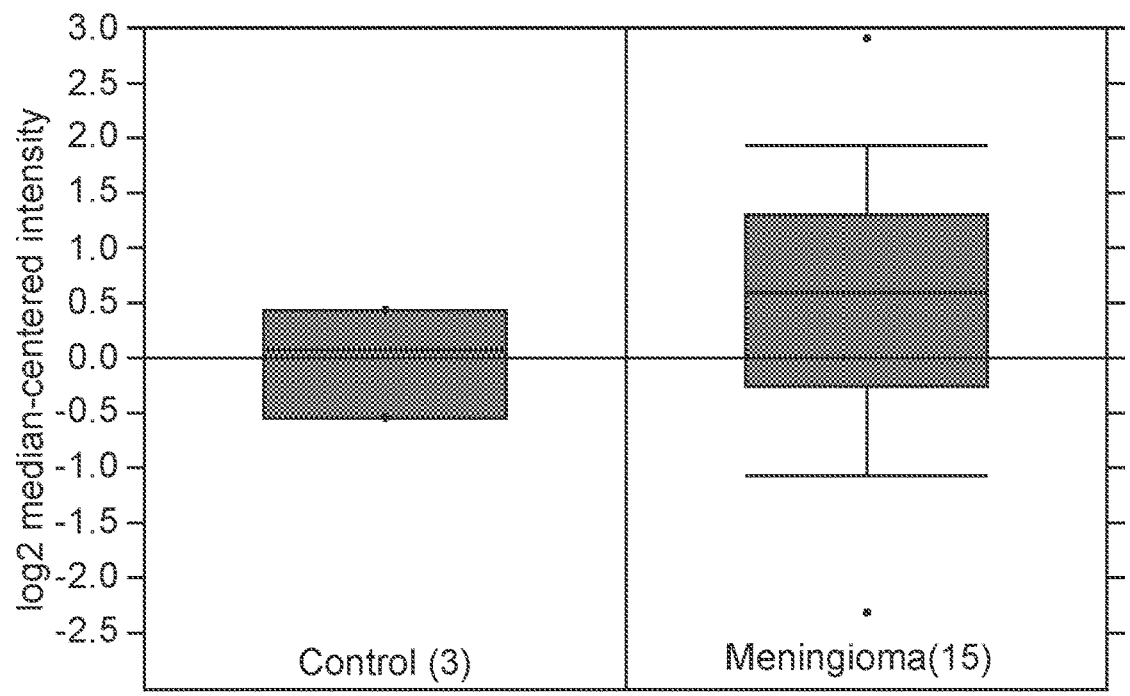

The ONCOMINE™ research platform (Compendia Bioscience, Ann Arbor, Mich., Thermo Fisher Scientific Inc) was used to analyze AR RNA amplification from several databases. Analysis of the TCGA database demonstrated a 1.74 fold AR RNA induction in GBMs (n=542) compared to normal brain (n=10) ($p=1.05\textasciicircum 10^{-6}$ Rank, 1861) (FIG. 2B). Analysis of the Murat cohort (Murat, Migliavacca et al. 2008) demonstrated a 1.44 fold AR RNA induction ($p=1.5810^{-7}$, Rank 660) in GBMs (n=80) compared to normal brain ("Control", n=4) (FIG. 2C). Analysis of the in Sun cohort (Sun, Hui et al. 2006) revealed that besides GBM (n=81) (fold change=2.12, $p=7.13\textasciicircum 10^{-17}$, Rank 322), overexpression of AR is seen also in other gliomas such as anaplastic astrocytoma (n=19) (fold change 2.282, $p=5.11\textasciicircum 10^{-7}$, Rank 625), Diffuse Astrocytoma (n=7) (fold change=1.511, p=0.010, rank 495) and oligodendroglioma (n=50) (fold change=1.744, $p=7.47\textasciicircum 10^{-10}$, Rank 660), compared to normal brain ("Brain", n=23) (FIG. 2D). This overexpression was also demonstrated in meningioma using the Watson cohort (Watson, Gutmann et al. 2002), including 3 normal brains (Control) and 15 meningiomas (FIG. 2E).

Figure 2F:
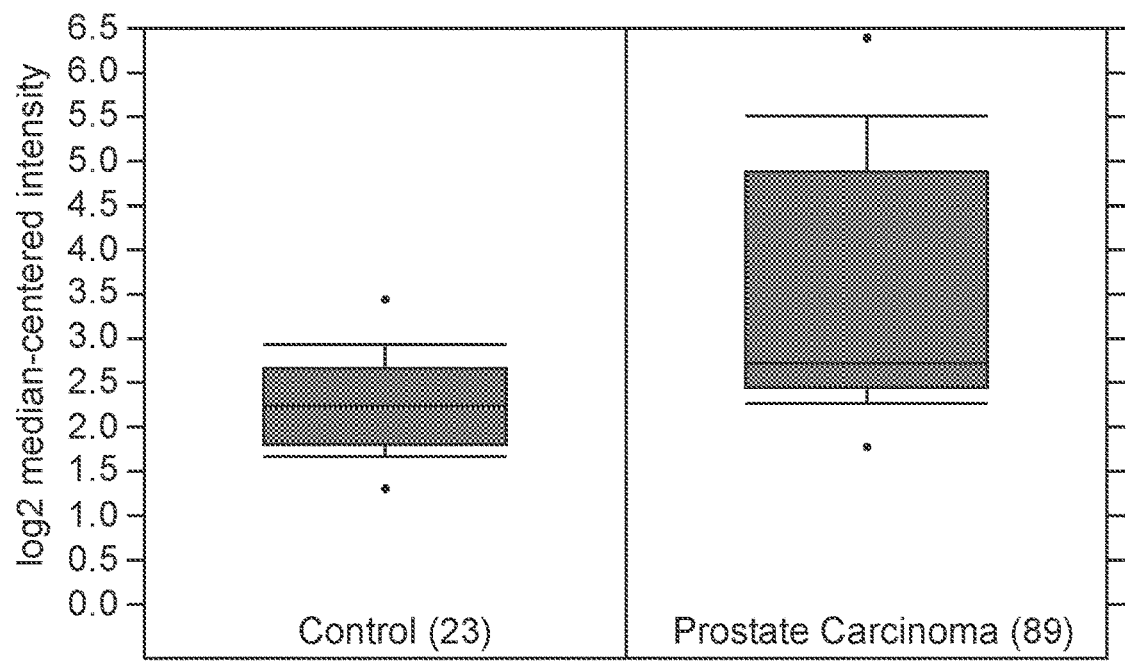
Figure 2G:
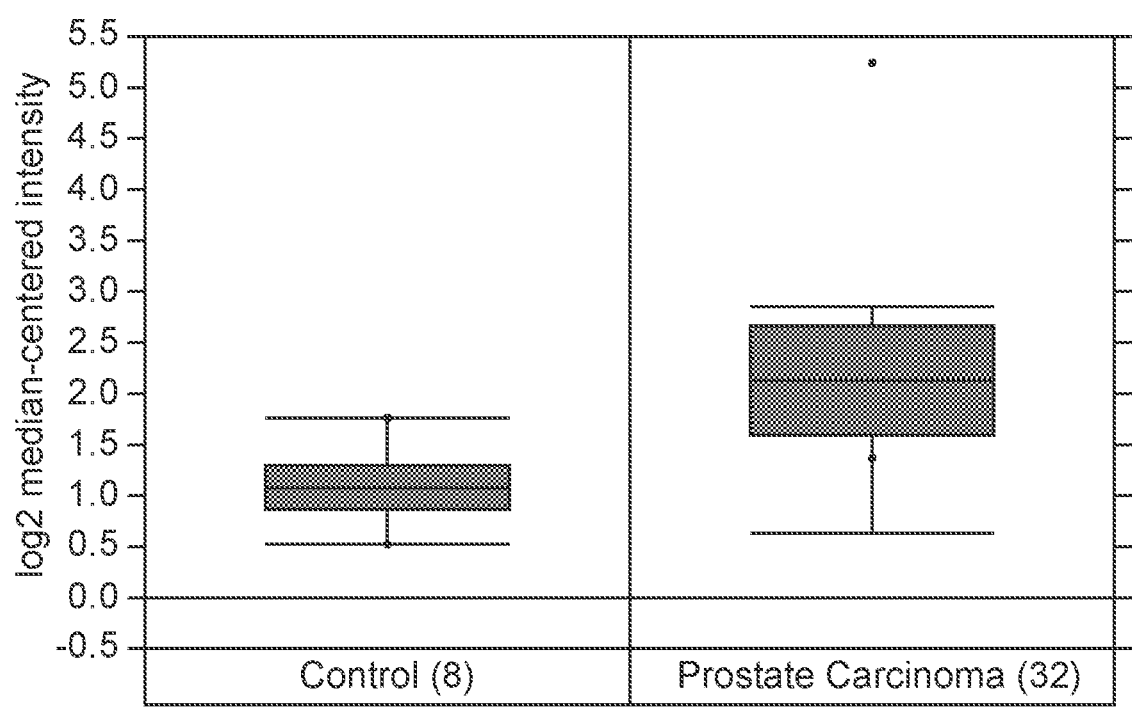

Using the Yu (Yu, Landsittel et al. 2004) and Vanaja (Vanaja, Cheville et al. 2003) databases, AR expression in prostate carcinoma (adenocarcinoma, n=89 and 32 respectively) was compared to normal tissue ("control", n=23 and 8 respectively). The results of this analysis have demonstrated a fold change of 1.88 and 1.4, $p=4.42\textasciicircum 10^{-5}$ and $5.09\textasciicircum 10^{-4}$, Rank=467 and 631 respectively (FIGS. 2F-2G). Thus, the over-expression levels in brain tumors and prostate cancer were surprisingly found to be similar (compare FIGS. 2B-2E to FIGS. 2F-2G).

Example 4. Antagonizing AR in Glioma Cell Lines

Figure 4A:
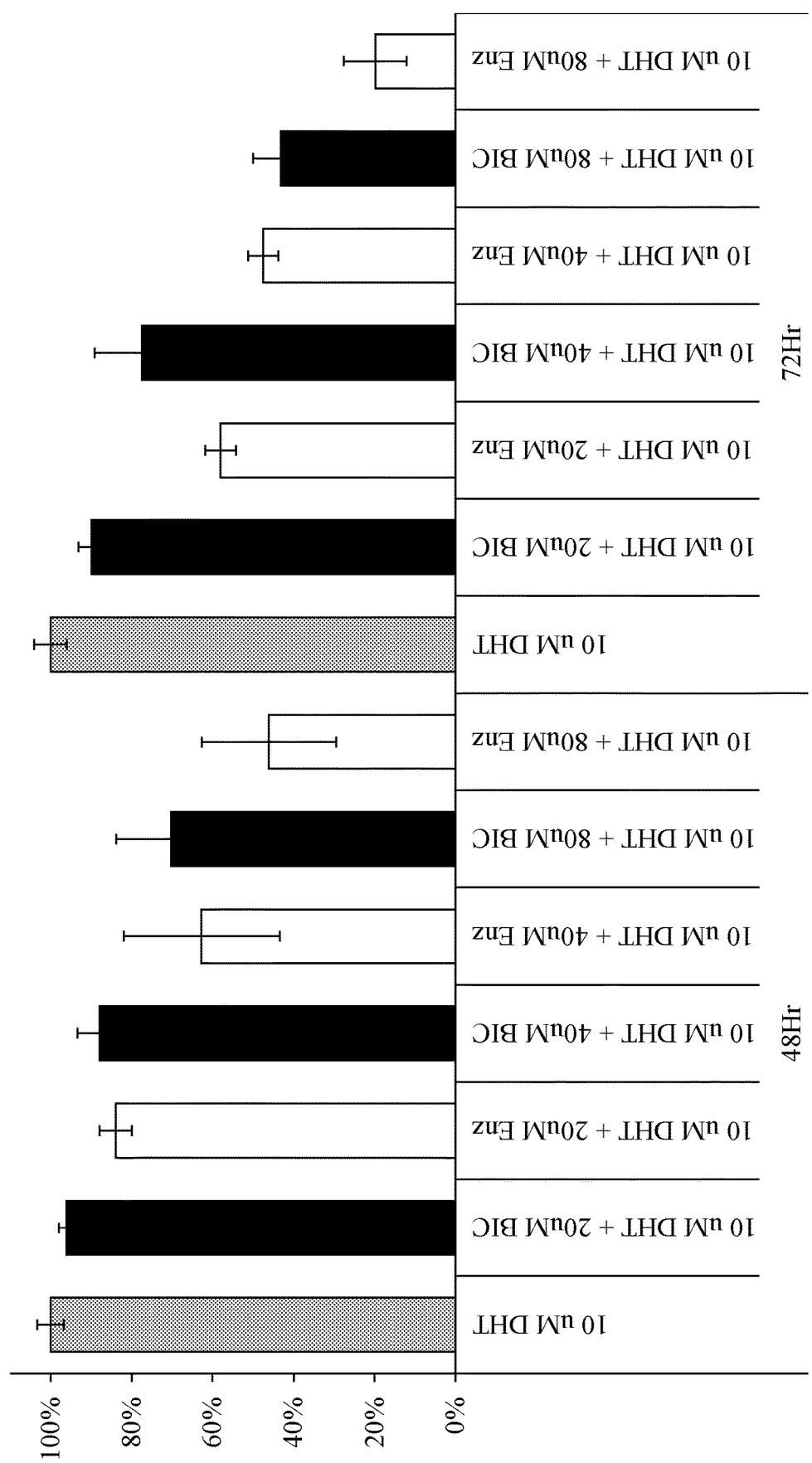
FIGS. 4A-4F. The effect of two AR antagonists, bicalutamide and enzalutamide on cell survival of three glioma cell lines (A172, U87MG and T98G).
Figure 4B:
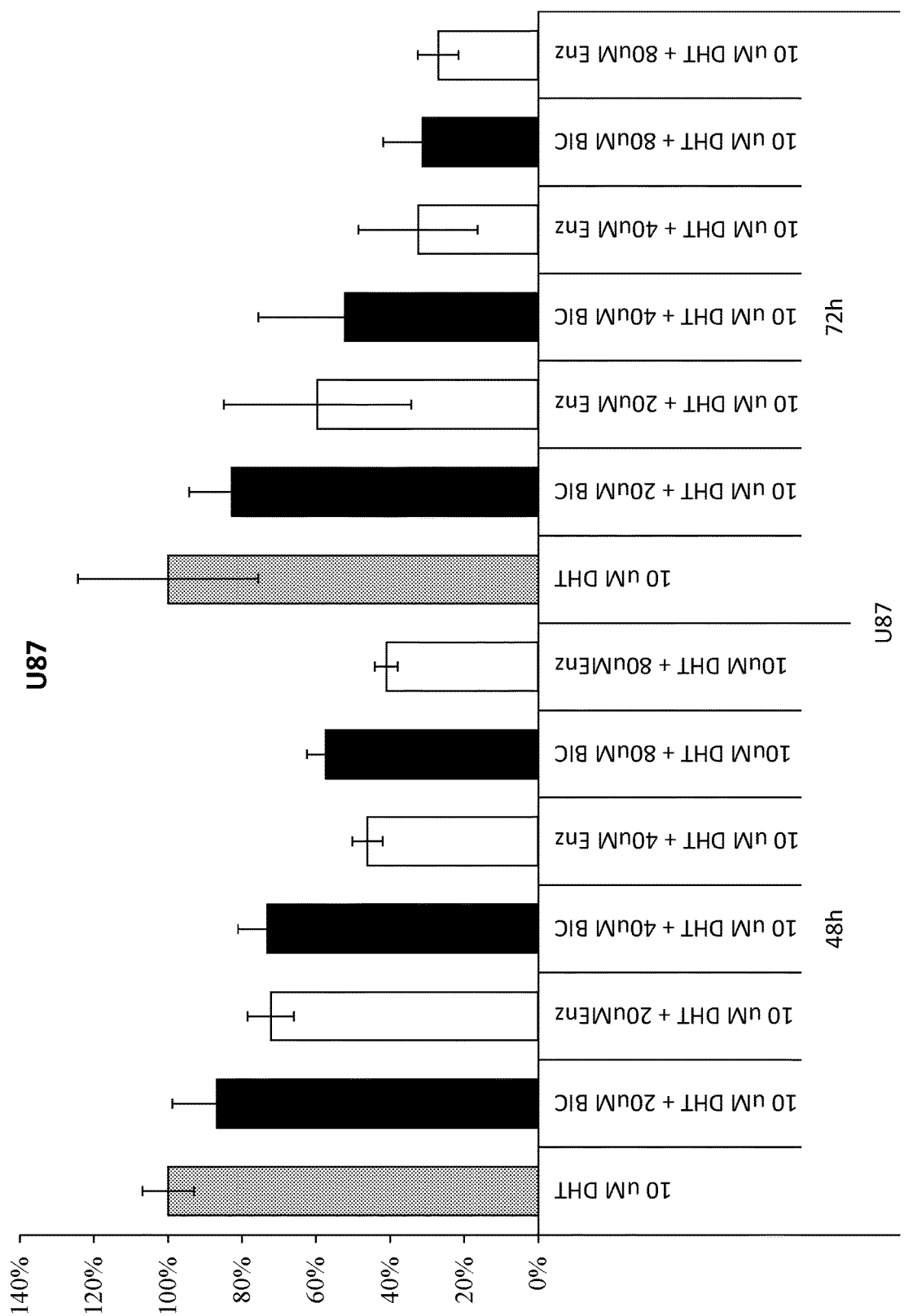
Figure 4C:
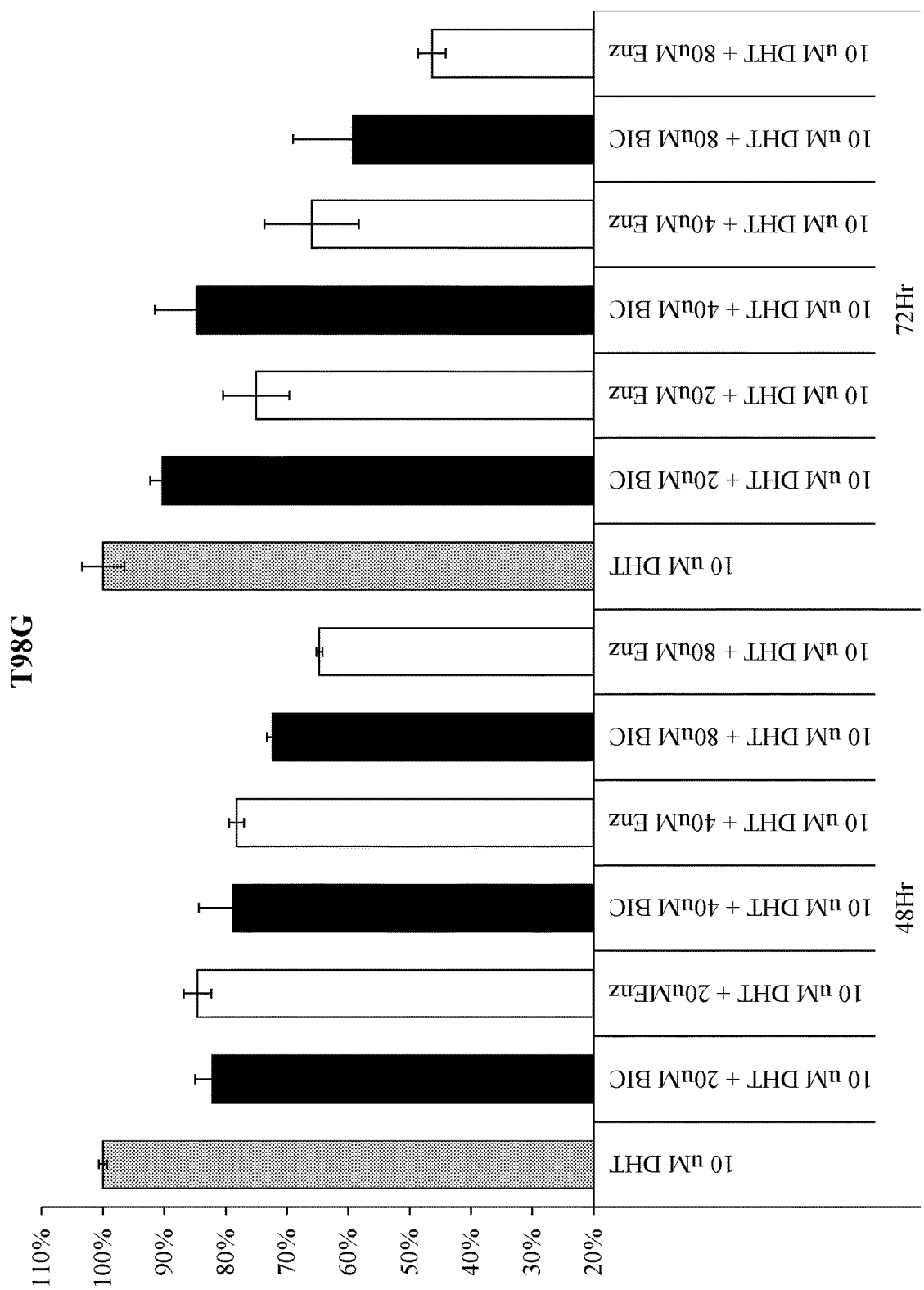
Figure 4D:
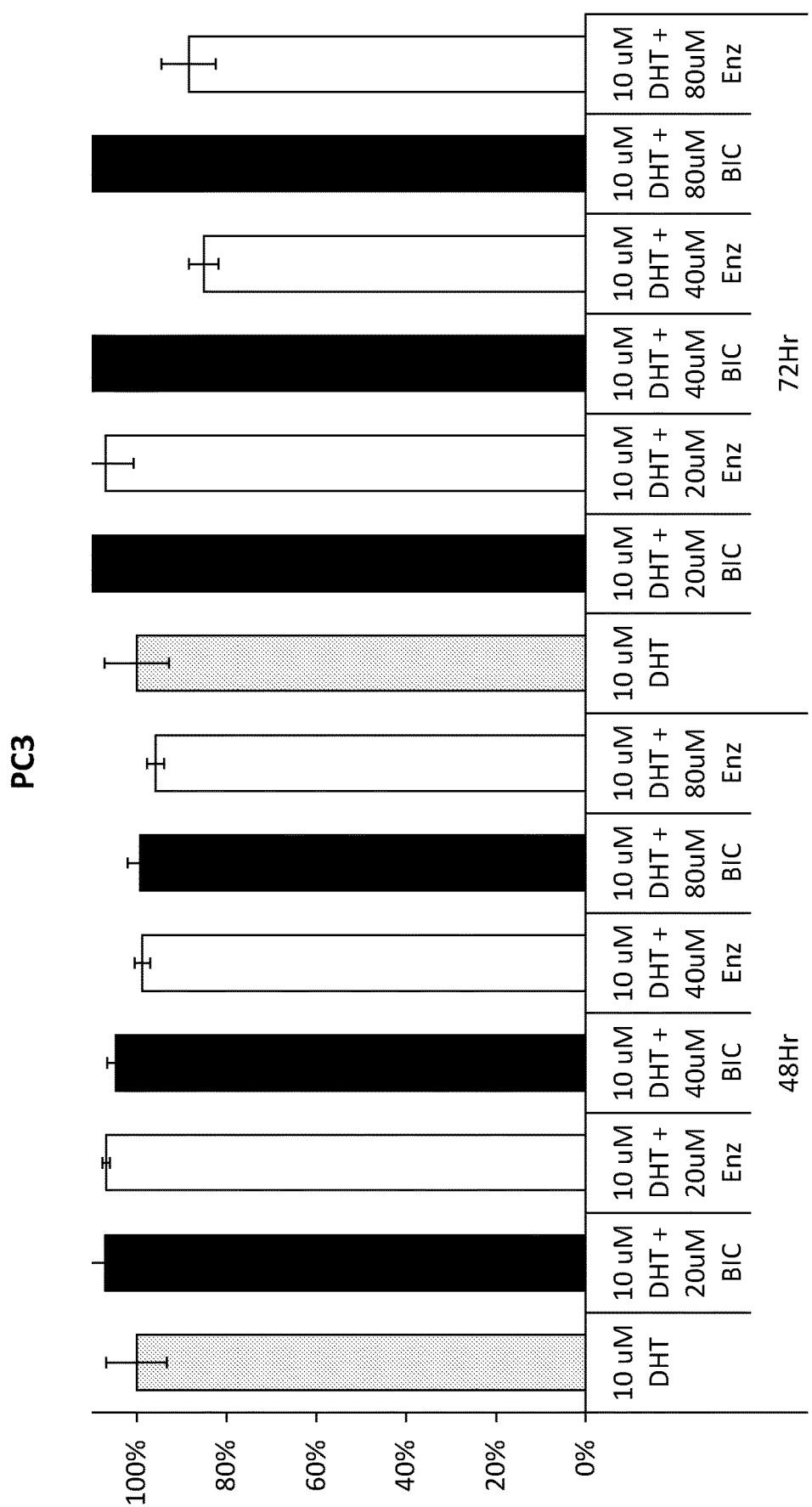
Figure 4E:
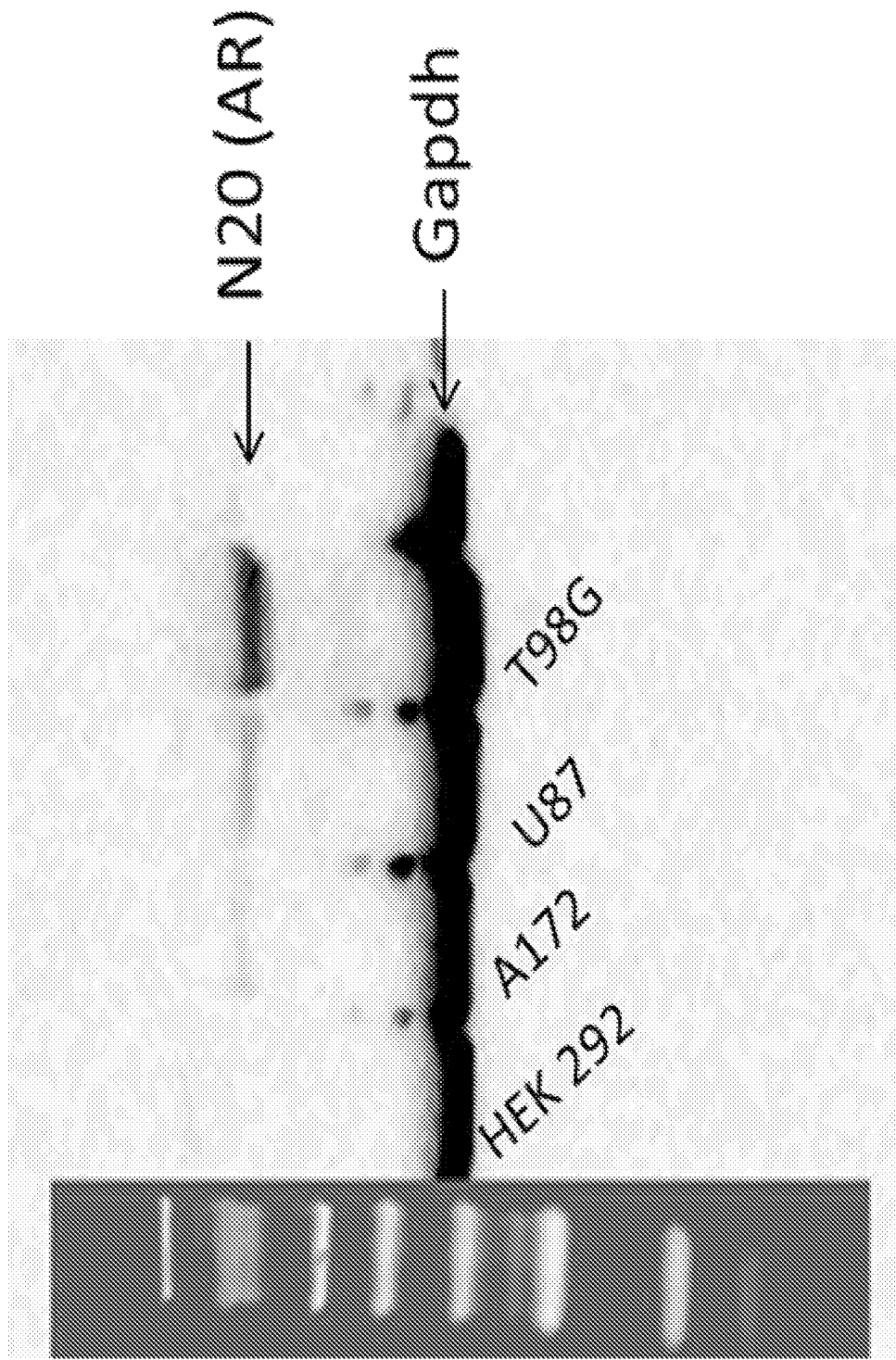

The effect of two AR antagonists, bicalutamide and enzalutamide on cell survival was tested in three glioma cell lines (A172, U87MG and T98G). The results, presented in FIGS. 4A-C, respectively, demonstrate that these two inhibitors reduce cell viability in a dose-dependent manner. In the experiments depicted in FIGS. 4A-C, cells were treated with DHT alone (grey bars) or in combination with 20 μM, 4004 or 80 μM of bicalutamide (BIC, black bars) or enzalutamide (ENZ, white bars with blacks dots) (X axis), for 48 hr (left) and 72 hr (right). Cell viability was determined by Crystal Violet assay and expressed as percentage of cell treated with DHT (Y axis). At 72 hrs following treatment, viability ranged from 90% at 20 uM (04) to 43% at 80 uM; 83% at 20 uM to 31% at 80 uM and 90% at 20 uM to 59% at 80 uM in bicalutamide-treated A172, U87MG and T98G cells, respectively. In Enzalutamide-treated cells, viability ranged from 58% at 20 uM to 20% at 80 uM; 60% at 20 uM to 27% at 80 uM and 75% at 20 uM to 46% at 80 uM in A172, U87MG and T98G cells respectively (FIGS. 4A-C respectively). The prostate carcinoma cell line PC3 that does not express AR or its variants was used as a negative control (FIG. 4D), in which white bars represent cells treated with DHT and different concentrations of enzalutamide. As can be seen in FIG. 4D, no significant effect was observed in these cells. Thus, enzalutamide demonstrated a higher efficacy rate compared to bicalutamide in all glioma tested cell lines (FIGS. 4A-4D). The effect of enzalutamide was found to be inversely correlated to the expression level of AR protein within the examined ranges (FIG. 4E).

Figure 4F:
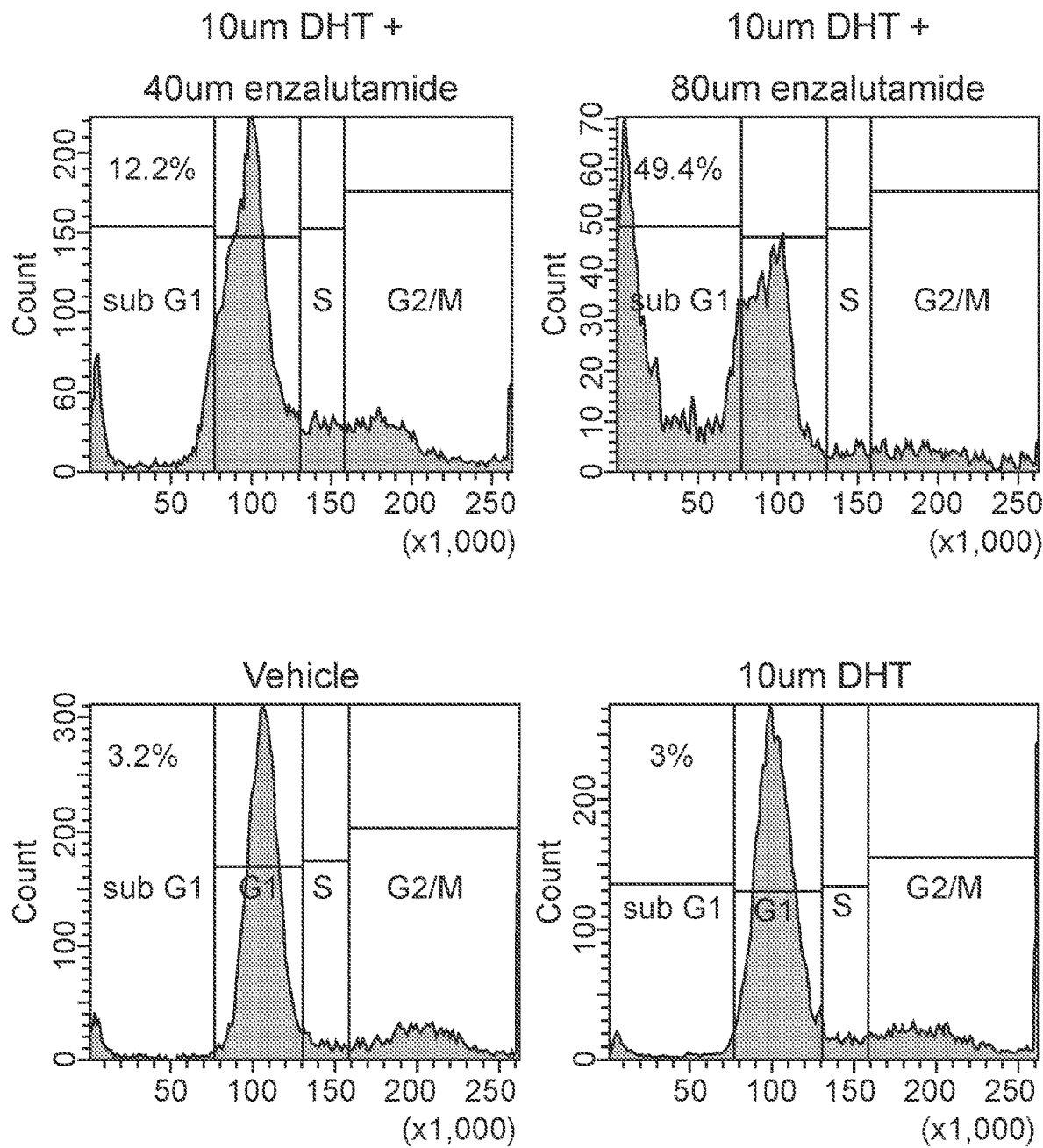

A cell cycle analysis of glioma cells treated with Enzalutamide demonstrated a dose dependent number of cells in sub-G1 phase, suggesting apoptosis as the mechanism for cell death (FIG. 4F).

Example 5. AR Splice Variant Lacking the Ligand Binding Domain in GBMs

Figure 5:
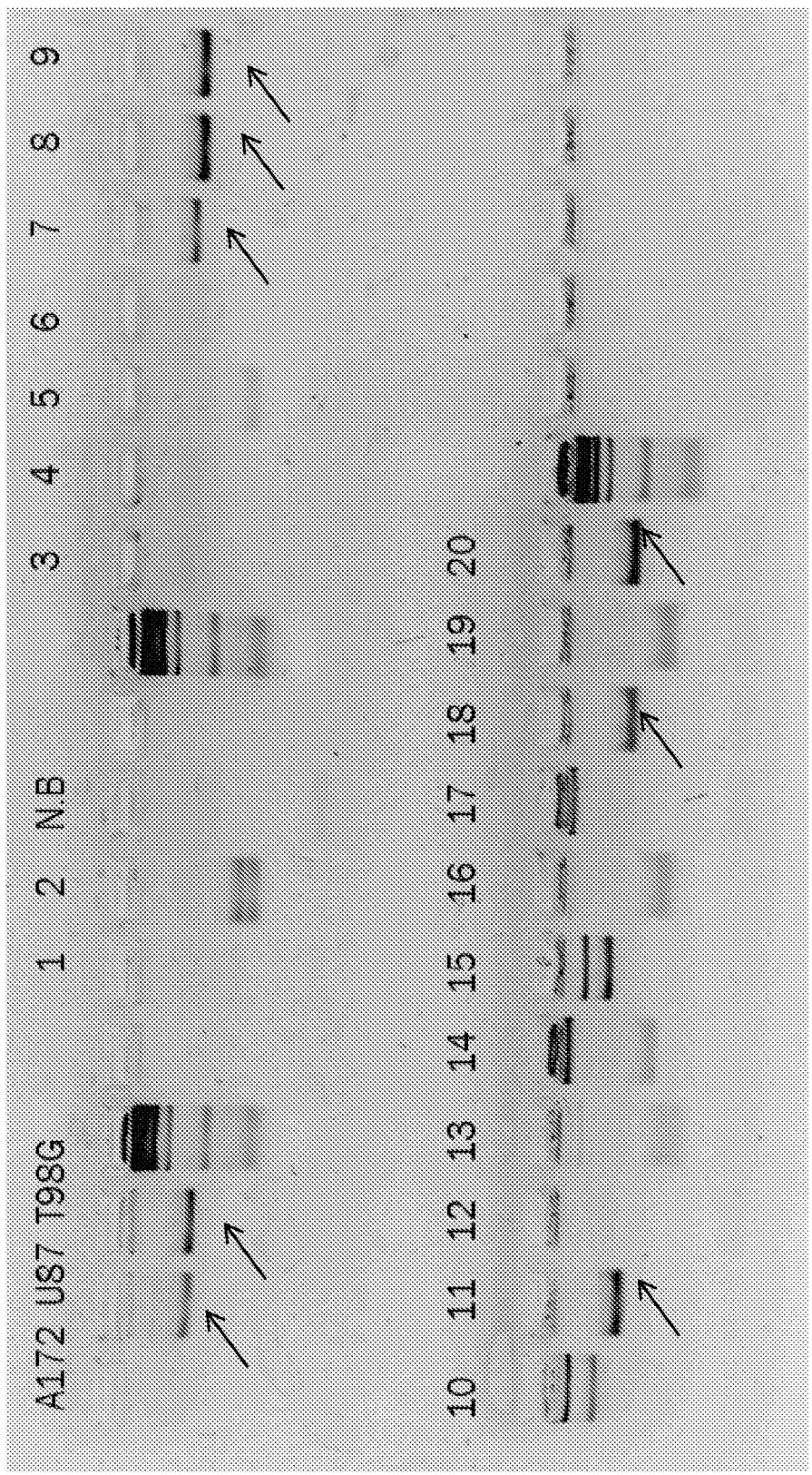
FIG. 5. GBM express in addition to the wild type AR the AR splice variant 7 which lack the LBD. AR variant 7 (A3) was analyzed by qPCR on 20 GBM specimens. The resulting 125 bp fragments were electrophoresed on 3.5% metaphor and visualized by Ethidium bromide staining (marked with arrows).

Next, a qPCR assay was conducted to examine the expression of AR variant mRNA in glioblastoma samples (1-20) and glioma cell lines (U87MG, T98G, and A172). As can be seen in FIG. 5, 30% of the tumors were found to express a splice variant lacking the ligand binding domain (variant 7), in addition to expression of the wild-type allele. Glioma cell lines U87MG and T98G, but not A172, were found to express a variant allele. N.B—normal brain sample.

Example 6. Combination Therapy with AR Inhibitors and EGFR Inhibitors

Figure 6A:
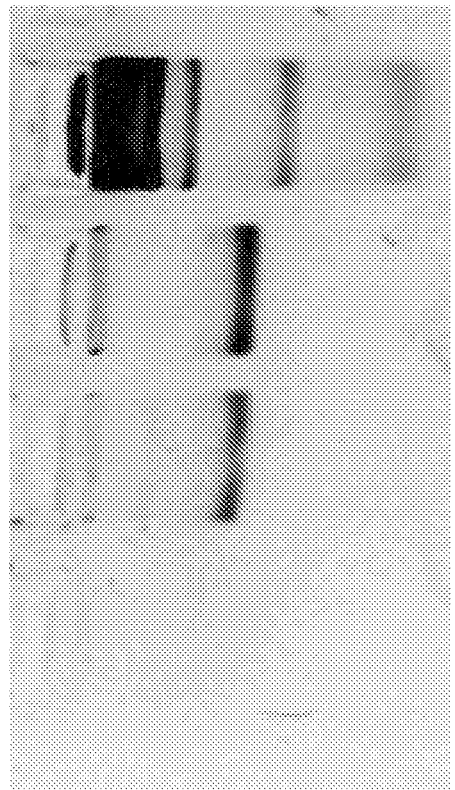

The effect of combination therapies that involve anti-AR signaling agents together with agents that target EGFR on AR modulation was examined in glial tumor cells expressing a ligand independent AR splice variant. For that purpose, T98G cells, expressing high levels of AR variant 7 (FIG. 6A) and high levels of EGFR (12.8 induction fold) were treated for 72 Hr with elevating concentrations of erlotinib (TARCEVA®) or Cetuximab (ranging from 1.25-10 μm) with or without addition of 20 μm of bicalutamide.

Figure 6B:
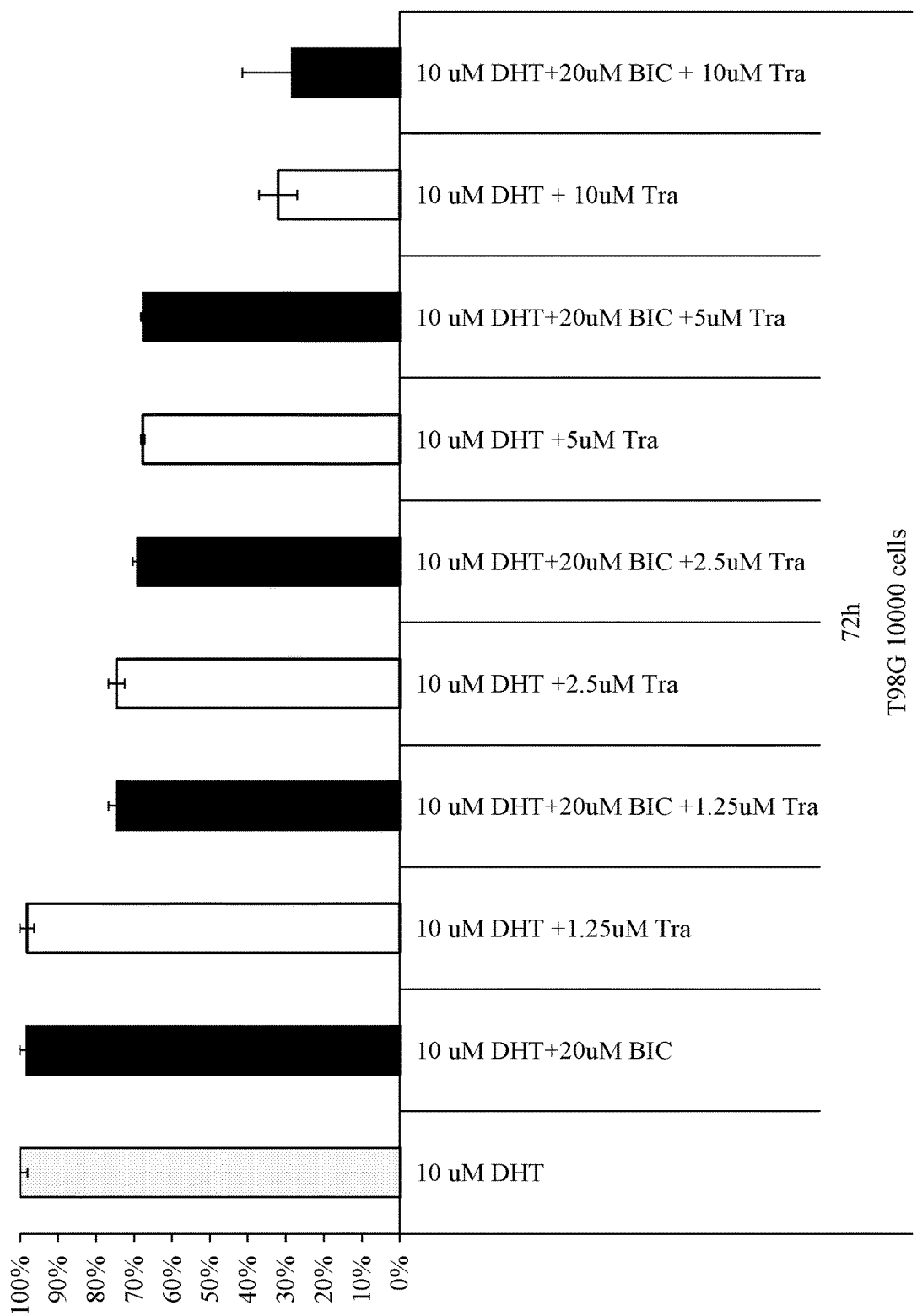

Cetuximab had no influence on the viability of T98G cells in this test system, either alone or in the combined therapy. This may be attributed to altered activity of Cetuximab in vivo compared to its activity in vitro, as previously reported. Specifically, it has been suggested that unlike small molecule inhibitors, the anti-tumor activity of Cetuximab may require immune-mediated mechanisms or other factors in the in vivo tumor microenvironment. In contradistinction, as shown in FIG. 6B, the combined therapy of erlotinib and bicalutamide was more efficient than each drug as single agent against these cells (cell viability of 94% at 1.25 μM and 63% at 10 μM with erlotinib alone and 76% and 31% respectively in the combined therapy) and acted in a synergistic manner.

Figure 6C:
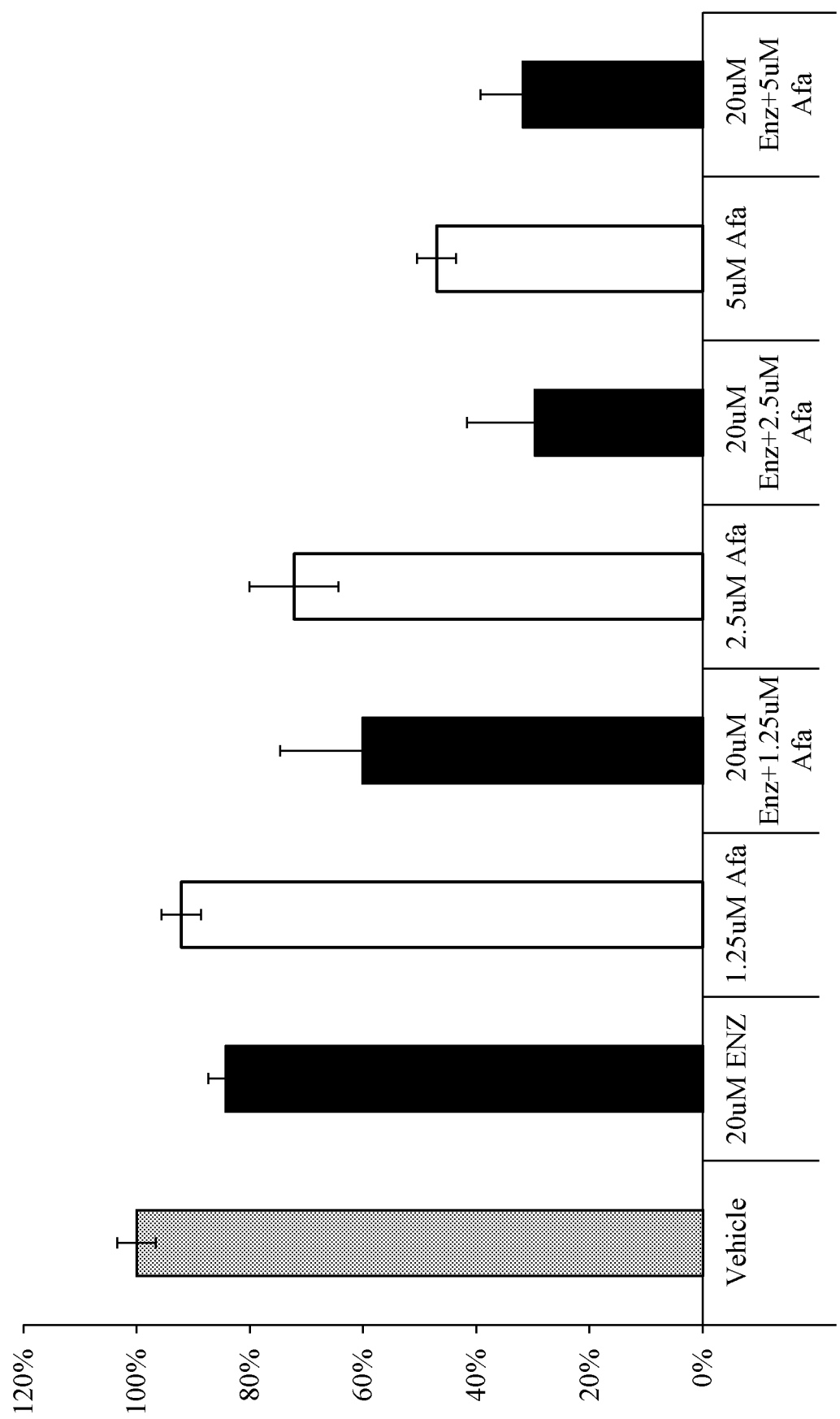

Similar experiments were performed with elevating concentrations of afatinib (ranging from 1.25-5 μm) with or without the addition of 20 μm of enzalutamide. The results, depicted in FIG. 6C, demonstrate that the combination of afatinib and enzalutamide was more effective in reducing cell viability than each agent alone (cell viability of 92% at 1.25 μM and 47% at 5 μM with afatinib alone and 57% and 30% respectively in the combined therapy), and exhibited a synergistic effect.

Figure 6D:
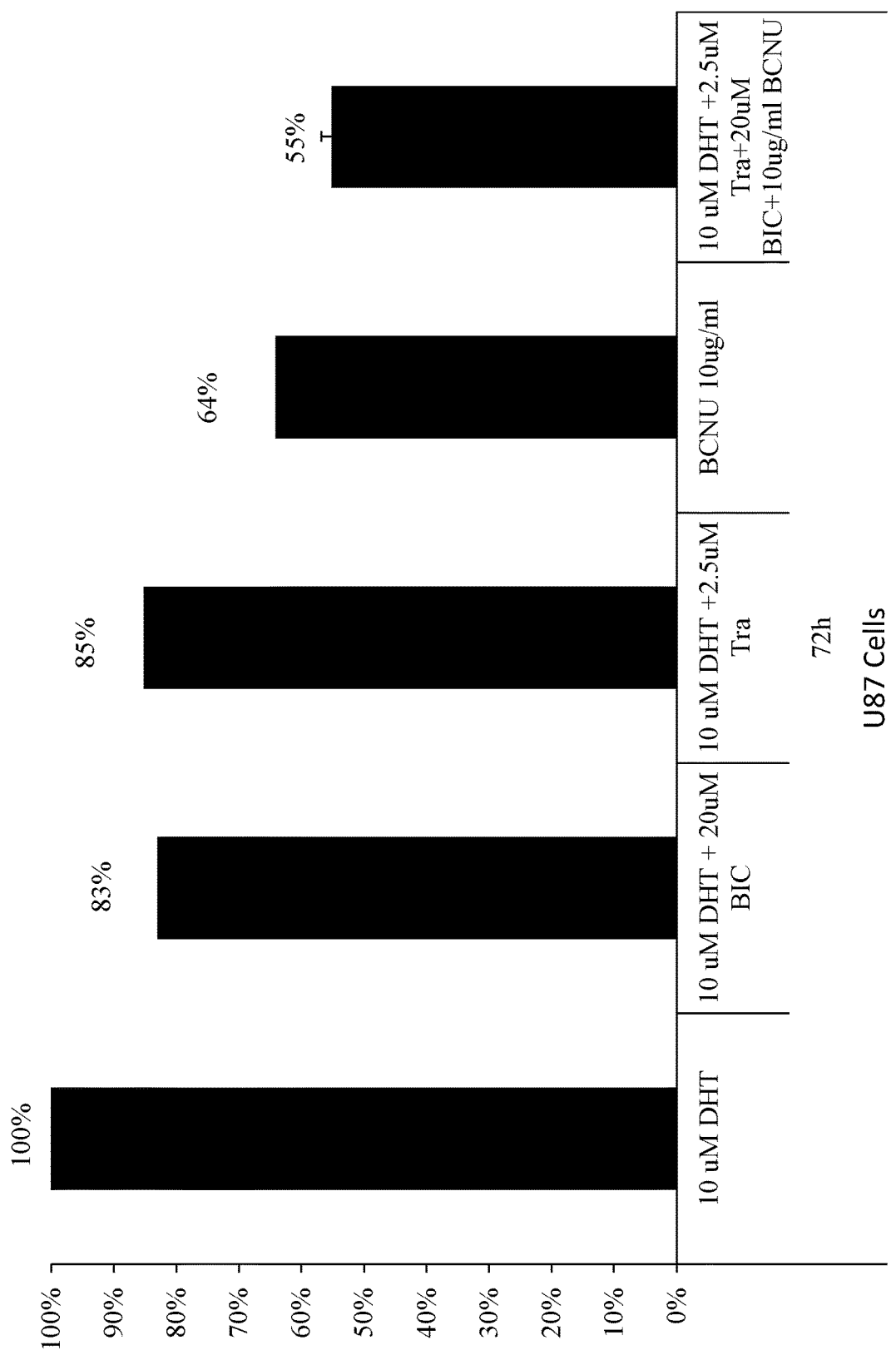

As can be seen in FIG. 6D, combination therapy of minimal concentrations of the alkylating agent BCNU with erlotinib and bicalutamide also yielded better results than each drug as monotherapy in U87MG cells, expressing moderate levels of AR7.

Taken together, the results presented herein demonstrate involvement of AR in GBM in patients of both sexes, and present a foundation for androgen-deprivation-therapy in particular in molecularly-selected therapeutic combinations as adjunctive to standard treatment.

Example 7. Animal Experiments

To test the efficacy of AR antagonists such as Enzalutamide in reducing the growth of glioblastoma in laboratory animals, glioma cells are implanted either subcutaneous or intracranial as xenografts into NOD mice (if using human tumors), or as grafts (if using mouse tumors) and tumor development is monitored.

Animal experiments are performed in accordance with the recommendations in the Guide for the Care and Use of Laboratory Animals, NIH. The protocol was approved by the Ethics of Animal Experiments Committee of the Hebrew University Medical School. Glioma cells are injected to 6- to 8-week old athymic nude (nu/nu) or c57bl/6 female mice either subcutaneous (SC) or Intracranial. In the SC group mice, tumor cells are injected into the right hind limb in a volume of 100 µl PBS and tumor growth is monitored with hand-held Vernier calipers (Scientific Products, McGraw, Ill.) twice a week until the tumors at the control group reaches 1500 mm$^3$ (length×width×thickness/2). In the intracranial injected group, tumor cells are injected to the right cerebral hemisphere (1 mm posterior and 2.3 mm lateral to the bregma, to a depth of 3 mm) in order to establish a brain tumor model. In this group the endpoint is considered as the number of days that elapsed from tumor implantation to the day of overt symptoms (significant weight loss, lethargy or hunched posture).

Test drugs are dissolved in 2% DMSO in PBS and injected intraperitoneally (IP). Each group of mice (n=7) is treated daily for 28 consecutive days with 1, 10, or 50 mg/kg enzalutamide, or bicalutamide or vehicle control. The dose of enzalutamide is established, and compared to combination therapy of enzalutamide with EGFR inhibitors. For that purpose, mice are treated daily for 28 consecutive days with 2.5, 5, or 10 mg/kg Afatinib with or without a daily dose of enzalutamide.

Example 8. The Efficacy of Anti Androgen Therapy on U87MG Human Glioblastoma Xenografts In Vivo Aathymic nude mice were inoculated subcutaneously with 5×10$^6$ glioblastoma cells (U87MG) into the interscapular area. Tumor growth was monitored with hand-held Vernier caliper twice a week. Tumor volume was estimated by calculation using the formula: (width$^2$×length)/2. On day 7 when the tumors reached an average volume of about 50 mm$^3$, mice were randomized into two treatment groups based on caliper measurements. All mice were treated three time per week by oral gavage using either 20 mg/kg Enzalutamide (XTANDI®, purchased from Astellas pharma, n=8) or vehicle (220 mg/Kg caprylocaproyl polyoxylglycerides in Saline, n=18). Mice were sacrificed when their tumor reached a size of 800-1000 mm$^3$ as requested by the local animal committee in order to minimize mice suffering. The results are presented in FIG. 7, in which each point represents the median tumor size±SEM shown with polynomial curve fitting.

Figure 7:
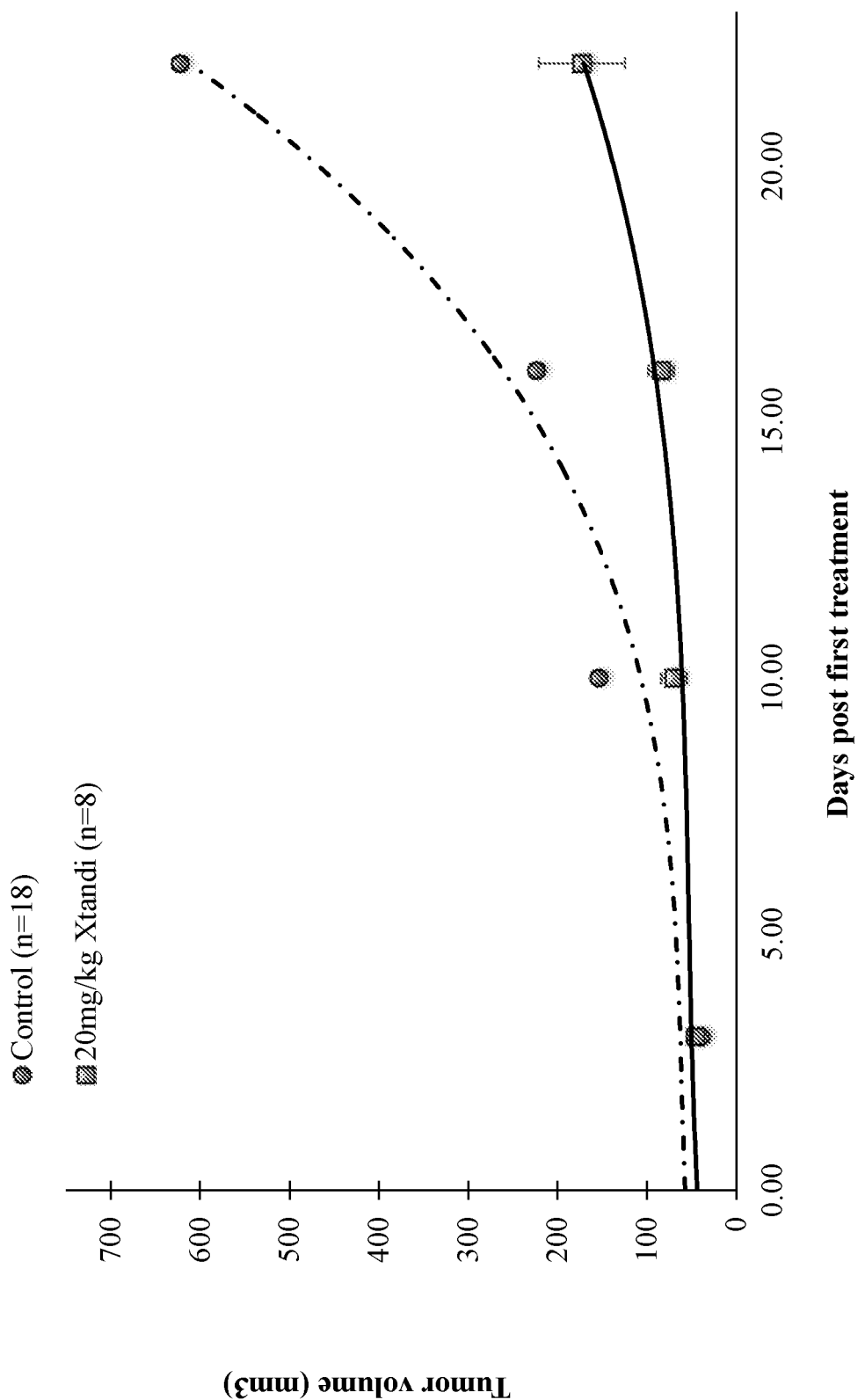
FIG. 7. In-vivo efficacy of anti-androgen (Enazlutamide—XTANDI®) therapy in U87MG human glioblastoma xenografts. Each point represents the median tumor size±SEM.

As can be seen in FIG. 7, mice treated with Enzalutamide exhibited significantly smaller tumors than the vehicle treated group (p<0.01). Thus, Enzalutamide was demonstrated to be markedly effective in treating xenograft glioblastoma tumors in vivo.

Example 9. In-Vivo Efficacy of Enzalutamide and Combination Therapy on Intracranial Implanted Tumors 6- to 8-week old athymic nude (nu/nu) mice are injected with the established amount of U87MG glioma cells. After 5 days when the tumor have been established, the tumor-bearing mice are randomized into 3 treatment groups (n=10 per group) and each group is treated by oral gavage for 28 consecutive days either with vehicle (control group) or with 25 or 50 mg/kg of enzalutamide Mice are sacrificed on the appearance of overt symptoms (significant weight loss, lethargy, hunched posture or other neurological signs). The endpoint is considered as the number of days that elapsed from tumor implantation to the day of overt symptoms.

Next, combination therapy of enzalutamide with EGFR inhibitors or alkylating agents is evaluated in this model. For that purpose, a group of 70 tumor bearing mice (established as described above) is randomized into treatment groups, mice are treated for 28 consecutive days with vehicle or with 2.5, 5, or 10 mg/kg afatinib with or without a consecutive one dose of enzalutamide, or with 25, 50, 100 or 200 mg/Kg temozolomide with or without a consecutive one dose of enzalutamide. The endpoint is considered as described above.

REFERENCES

Bassetto M, et al. (2016). Eur J Med Chem. Aug. 8; 118:230-43.
Bing L, et al. (2015). Neurochem Res 40: 41-48.
Carroll R S, et al. (1995). Neurosurgery 37: 496-503; discussion 503-494.
Carroll R S, et al. (1995b). J Neurosurg 82:453-460.
Chung Y G, et al. (1996). J Korean Med Sci 11: 517-521.
Davey, R. A., & Grossmann, M. (2016). The Clinical Biochemist Reviews, 37(1), 3-15.
Gatson J W, Singh M (2007). Endocrinology 148: 2458-2464.
Hickey T E, et al. (2015). Oncotarget. 6(42):44728-44744.
Kerkhof et al., (2013). Epilepsia, 54(Suppl. 9):12-17.
Lee et al. (2016). Clin Cancer Res; 22(13); 3124-6.
Lu et al. (2013). Transl Androl Urol; 2(3):178-186.
Maxwell, et al. (1993). J Neurosurg 78:456-462.
Murat A, et al. (2008). J Clin Oncol 26: 3015-3024.
Reardon D A, et al. (2015). Neuro Oncol. March; 17(3): 430-9.
Rodriguez-Vida et al. (2015). Drug Design, Development and Therapy 9, 3325-3339.
Sun L, et al. (2006). Cancer Cell 9: 287-300.
Tan M H, et al. (2015). Acta Pharmacol Sin 36: 3-23.
Vanaja D K et al. (2003). Cancer Res 63: 3877-3882
Wadosky, K. M. and S. Koochekpour (2016). Int J Biol Sci 12(4): 409-426.
Watson, M. A., D. H. Gutmann, et al. (2002). Am J Pathol 161(2): 665-672.
Wick, Weller et al. 2011
Wick, W., M. Weller, et al. (2011). Neuro Oncol 13(6): 566-579.
Yu, X., Y. Jiang, et al. (2015). Tumour Biol 36(2): 967-972.
Yu, Y. P., D. Landsittel, et al. (2004). J Clin Oncol 22(14): 2790-2799.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating a glial tumor characterized by AR expression in at least a portion of the tumor cells in a human subject in need thereof, comprising administering to the subject, a therapeutic combination in which the active ingredients consist of:
   (i) at least one AR antagonist or inhibitor selected from the group consisting of enzalutamide, bicalutamide and apalutamide and
   (ii) at least one anti-cancer agent selected from the group consisting of an alkylating agent and a quinazoline EGFR inhibitor,
   wherein the alkylating agent is selected from the group consisting of: nitrogen mustard N-oxide, cyclophosphamide, ifosfamide, melphalan, busulfan, mitobronitol, carboquone, thiotepa, ranimustine, nimustine, temozolomide and carmustine,
   and the quinazoline EGFR inhibitor is erlotinib or afatinib.

2. The method of claim 1, wherein said therapeutic combination is in the form of a pharmaceutical composition comprising the at least one AR antagonist or inhibitor and the at least one anti-cancer agent.

3. The method of claim 1, wherein the AR antagonist or inhibitor is enzalutamide or bicalutamide, and the alkylating agent is selected from the group consisting of temozolomide and carmustine.

4. The method of claim 1, wherein said tumor is a glioma selected from the group consisting of glioblastoma, anaplastic astrocytoma, diffuse astrocytoma, oligodendroglioma, anaplastic oligodendroglioma, oligoastrocytoma and anaplastic oligoastrocytoma, or wherein said subject is female.

5. The method of claim 1, wherein said tumor is characterized by amplification at the AR gene locus, loss of heterozygosity (LOH) at the AR gene locus, AR overexpression associated with 1.1-20 fold elevation of the AR protein level, and/or expression of a ligand-independent AR splice variant, in at least a portion of the tumor cells.

6. The method of claim 1, wherein said tumor is characterized by amplification at the AR gene locus associated with AR gene copy number increase of 1-20 or by LOH at the AR gene locus, in at least a portion of the tumor cells.

7. The method of claim 1, wherein said tumor is characterized by expression of AR variant 7 (AR-V7).

8. The method of claim 7 wherein said tumor is characterized by over-expression of wild-type AR and by expression of AR-V7 in at least a portion of the tumor cells, or wherein said tumor is characterized by over-expression of wild-type AR and over-expression of AR-V7 in at least a portion of the tumor cells.

9. The method of claim 7 wherein said tumor is characterized by expression of AR-V7 and is further characterized by LOH at the AR gene locus, in at least a portion of the tumor cells.

10. The method of claim 1, wherein the tumor is anaplastic astrocytoma, and the therapeutic combination contains, as the active ingredients, enzalutamide or bicalutamide as the AR antagonist, and temozolomide, carmustine, afatinib and/or erlotinib as the at least one anti-cancer agent.

11. The method of claim 1, wherein the AR antagonist is bicalutamide, the alkylating agent is carmustine or temozolomide and the quinazoline EGFR inhibitor is erlotinib or afatinib, or wherein the AR antagonist is enzalutamide and the quinazoline EGFR inhibitor is afatinib.

12. The method of claim 10, wherein the combination is selected from the group consisting of:
(i) bicalutamide and erlotinib,
(ii) bicalutamide, carmustine and erlotinib, and
(iii) enzalutamide and afatinib.

* * * * *

SEQUENCE LISTING

<160> NUMBER OF SEQ ID NOS: 12

<210> SEQ ID NO 1
<211> LENGTH: 920
<212> TYPE: PRT
<213> ORGANISM: Homo sapiens

<400> SEQUENCE: 1

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
                100                 105                 110

Glu Gln Gln Pro Ser Gln Pro Gln Ser Ala Leu Glu Cys His Pro Glu
            115                 120                 125

Arg Gly Cys Val Pro Glu Pro Gly Ala Ala Val Ala Ala Ser Lys Gly
130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Glu Ala Val Ser Glu Gly Ser Ser Ser
            195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
```

-continued

```
            325                 330                 335
Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
            355                 360                 365

Leu Ala Leu Ala Gly Pro Pro Pro Pro Pro Pro His Pro His
            370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                    405                 410                 415

Ala Gly Ala Ala Gly Pro Gly Ser Gly Ser Pro Ser Ala Ala Ala Ser
                    420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly
            450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                    485                 490                 495

Phe Thr Ala Pro Asp Val Trp Tyr Pro Gly Gly Met Val Ser Arg Val
                    500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
            530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                    565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                    645                 650                 655

Thr Gln Lys Leu Thr Val Ser His Ile Glu Gly Tyr Glu Cys Gln Pro
                    660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                    725                 730                 735

Val Ile Gln Tyr Ser Trp Met Gly Leu Met Val Phe Ala Met Gly Trp
                    740                 745                 750
```

```
Arg Ser Phe Thr Asn Val Asn Ser Arg Met Leu Tyr Phe Ala Pro Asp
            755                 760                 765

Leu Val Phe Asn Glu Tyr Arg Met His Lys Ser Arg Met Tyr Ser Gln
770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
                820                 825                 830

Met Asn Tyr Ile Lys Glu Leu Asp Arg Ile Ile Ala Cys Lys Arg Lys
                835                 840                 845

Asn Pro Thr Ser Cys Ser Arg Arg Phe Tyr Gln Leu Thr Lys Leu Leu
            850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
                900                 905                 910

Lys Pro Ile Tyr Phe His Thr Gln
            915                 920

<210> SEQ ID NO 2
<211> LENGTH: 644
<212> TYPE: PRT
<213> ORGANISM: Homo sapiens

<400> SEQUENCE: 2

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
            35                  40                  45

Pro Pro Gly Ala Ser Leu Leu Leu Leu Gln Gln Gln Gln Gln Gln Gln
        50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
                100                 105                 110

Glu Gln Gln Pro Ser Gln Pro Gln Ser Ala Leu Glu Cys His Pro Glu
            115                 120                 125

Arg Gly Cys Val Pro Glu Pro Gly Ala Ala Val Ala Ala Ser Lys Gly
        130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
                180                 185                 190

Leu Leu Gln Gln Gln Gln Gln Glu Ala Val Ser Glu Gly Ser Ser Ser
```

```
                195                 200                 205
Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Asn Phe Pro
        355                 360                 365

Leu Ala Leu Ala Gly Pro Pro Pro Pro Pro Pro His Pro His
370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
    530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620
```

Met Thr Leu Gly Glu Lys Phe Arg Val Gly Asn Cys Lys His Leu Lys
625                 630                 635                 640

Met Thr Arg Pro

<210> SEQ ID NO 3
<211> LENGTH: 19
<212> TYPE: DNA
<213> ORGANISM: Artificial Sequence
<220> FEATURE:
<223> OTHER INFORMATION: PCR primer

<400> SEQUENCE: 3
tgcgcgaagt gatccagaa                                                19

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tctgggacgc aacctctctc                                               20

<210> SEQ ID NO 5
<211> LENGTH: 18
<212> TYPE: DNA
<213> ORGANISM: Artificial Sequence
<220> FEATURE:
<223> OTHER INFORMATION: PCR primer

<400> SEQUENCE: 5
gtattgggcg cctggtca                                                 18

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
aggggtcatt gatggcaaca                                               20

<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
accgaggagc tttccagaat c                                             21

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
aggctctggg acgcaacct                                                19

```
<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
gatggtcaag gtcgcaagc                                                19

<210> SEQ ID NO 10
<211> LENGTH: 26
<212> TYPE: DNA
<213> ORGANISM: Artificial Sequence
<220> FEATURE:
<223> OTHER INFORMATION: PCR primer

<400> SEQUENCE: 10
atatcctaca acaaacttgt ctggaa                                        26

<210> SEQ ID NO 11
<211> LENGTH: 32
<212> TYPE: DNA
<213> ORGANISM: Artificial Sequence
<220> FEATURE:
<223> OTHER INFORMATION: PCR primer

<400> SEQUENCE: 11
ccatcttgtc gtcttcggaa atgttatgaa gc                                 32

<210> SEQ ID NO 12
<211> LENGTH: 26
<212> TYPE: DNA
<213> ORGANISM: Artificial Sequence
<220> FEATURE:
<223> OTHER INFORMATION: PCR primer

<400> SEQUENCE: 12
tttgaatgag gcaagtcagc ctttct                                        26
```